(12) United States Patent
Savage et al.

(10) Patent No.: US 8,036,743 B2
(45) Date of Patent: Oct. 11, 2011

(54) AUTOMATED OPTIMIZATION OF MULTI-ELECTRODE PACING FOR CARDIAC RESYNCHRONIZATION

(75) Inventors: George M. Savage, Portola Valley, CA (US); Todd Thompson, San Jose, CA (US); Mark J. Zdeblick, Portola Valley, CA (US); Lawrence W. Arne, Redwood City, CA (US); Olivier Colliou, Los Gatos, CA (US); Benedict James Costello, Berkeley, CA (US); Fataneh A. Omidvar, Danville, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 756 days.

(21) Appl. No.: 11/909,786

(22) PCT Filed: Mar. 31, 2006

(86) PCT No.: PCT/US2006/012246
§ 371 (c)(1),
(2), (4) Date: Jun. 5, 2008

(87) PCT Pub. No.: WO2006/105474
PCT Pub. Date: Oct. 5, 2006

(65) Prior Publication Data
US 2008/0294218 A1 Nov. 27, 2008

Related U.S. Application Data

(60) Provisional application No. 60/667,575, filed on Mar. 31, 2005, provisional application No. 60/667,529, filed on Mar. 31, 2005, provisional application No. 60/684,751, filed on May 25, 2005, provisional application No. 60/695,577, filed on Jun. 29, 2005.

(51) Int. Cl.
*A61N 1/39* (2006.01)

(52) U.S. Cl. .......................................................... 607/5
(58) Field of Classification Search .................. 607/4, 5, 607/17
See application file for complete search history.

(56) References Cited

U.S. PATENT DOCUMENTS 2,956,586 A   10/1960   Zeigler et al.
(Continued)

FOREIGN PATENT DOCUMENTS

EP            0659388      6/1995
(Continued)

OTHER PUBLICATIONS

Auricchio et al., "The Pacing Therapies for Congestive Heart Failure (PATH-CHF) Study: Rationale, Design and Endpoints of a Prospective Randomized Multicenter Study" Am J. Cardio.: 83:130D-135D (1999).

(Continued)

*Primary Examiner* — Scott Getzow
*Assistant Examiner* — Amanda Patton
(74) *Attorney, Agent, or Firm* — Bozicevic, Field & Francis LLP; Bret E. Field

(57) ABSTRACT

One embodiment of the present invention provides a system for automatically optimizing CRT procedures using a multi-electrode pacing lead. During operation, the system performs a first set of iterations to select one or more satellites on one or more pacing leads inserted in a patient. A pacing lead includes a plurality of pacing satellites, and a pacing satellite includes a plurality of electrodes that can be individually addressed and used for transmitting or detecting electric signals. The system then performs a second set of iterations to select one or more electrodes on the selected satellites. The system further performs a third set of iterations to select one or more timing configurations for pacing signals transmitted through one or more of the selected electrodes.

36 Claims, 26 Drawing Sheets

U.S. PATENT DOCUMENTS

| | | |
|---|---|---|
| 3,888,260 A | 6/1975 | Fischell |
| 3,985,123 A | 10/1976 | Herzlinger et al. |
| 4,164,946 A | 8/1979 | Langer |
| 4,262,982 A | 4/1981 | Kenny |
| 4,397,314 A | 8/1983 | Vaguine |
| 4,399,820 A | 8/1983 | Wirtzfeld et al. |
| 4,600,454 A | 7/1986 | Plummer |
| 4,603,705 A | 8/1986 | Speicher et al. |
| 4,628,934 A | 12/1986 | Pohndorf et al. |
| 4,628,935 A | 12/1986 | Jones et al. |
| 4,750,494 A | 6/1988 | King |
| 4,776,334 A | 10/1988 | Prionas |
| 4,815,472 A | 3/1989 | Wise et al. |
| 4,877,032 A | 10/1989 | Heinze et al. |
| 4,878,898 A | 11/1989 | Griffin et al. |
| 4,881,410 A | 11/1989 | Wise et al. |
| 4,902,273 A | 2/1990 | Choy et al. |
| 5,004,275 A | 4/1991 | Miller |
| 5,005,613 A | 4/1991 | Stanley |
| 5,035,246 A | 7/1991 | Heuvelmans et al. |
| 5,072,737 A | 12/1991 | Goulding |
| 5,111,816 A | 5/1992 | Pless et al. |
| 5,113,868 A | 5/1992 | Wise et al. |
| 5,156,154 A | 10/1992 | Valenta, Jr. et al. |
| 5,158,536 A | 10/1992 | Sekins et al. |
| 5,176,619 A | 1/1993 | Segalowitz |
| 5,188,106 A | 2/1993 | Nappholz et al. |
| 5,209,238 A | 5/1993 | Sundhar |
| 5,213,098 A | 5/1993 | Bennett et al. |
| 5,243,981 A | 9/1993 | Hudrlik |
| 5,285,744 A | 2/1994 | Grantham et al. |
| 5,304,208 A | 4/1994 | Inguaggiato et al. |
| 5,305,745 A | 4/1994 | Zacouto |
| 5,313,020 A | 5/1994 | Sackett |
| 5,391,199 A | 2/1995 | Ben-Haim |
| 5,411,532 A | 5/1995 | Mortazavi |
| 5,411,537 A | 5/1995 | Munshi et al. |
| 5,417,717 A | 5/1995 | Salo et al. |
| 5,419,767 A | 5/1995 | Eggers et al. |
| 5,423,323 A | 6/1995 | Orth |
| 5,433,198 A | 7/1995 | Desai |
| 5,509,411 A | 4/1996 | Littmann et al. |
| 5,535,752 A | 7/1996 | Halperin et al. |
| 5,544,656 A | 8/1996 | Pitsillides et al. |
| 5,549,650 A | 8/1996 | Bornzin et al. |
| 5,579,234 A | 11/1996 | Wiley et al. |
| 5,579,764 A | 12/1996 | Goldreyer |
| 5,591,142 A | 1/1997 | Van Erp |
| 5,593,430 A | 1/1997 | Renger |
| 5,628,777 A | 5/1997 | Moberg et al. |
| 5,662,587 A | 9/1997 | Grundfest et al. |
| 5,674,258 A | 10/1997 | Henschel et al. |
| 5,676,153 A | 10/1997 | Smith et al. |
| 5,683,429 A | 11/1997 | Mehra |
| 5,713,937 A | 2/1998 | Nappholz et al. |
| 5,720,768 A | 2/1998 | Verboven-Nelissen |
| 5,743,267 A | 4/1998 | Nikolic et al. |
| 5,751,050 A | 5/1998 | Ishikawa et al. |
| 5,788,647 A | 8/1998 | Eggers |
| 5,797,903 A | 8/1998 | Swanson et al. |
| 5,800,460 A | 9/1998 | Powers et al. |
| 5,800,465 A | 9/1998 | Thompson et al. |
| 5,810,735 A | 9/1998 | Halperin et al. |
| 5,814,089 A | 9/1998 | Stokes et al. |
| 5,836,987 A | 11/1998 | Baumann et al. |
| 5,873,849 A | 2/1999 | Bernard |
| 5,902,234 A | 5/1999 | Webb |
| 5,902,248 A | 5/1999 | Millar et al. |
| 5,913,814 A | 6/1999 | Zantos |
| 5,924,997 A | 7/1999 | Campbell |
| 5,935,084 A | 8/1999 | Southworth |
| 5,938,690 A | 8/1999 | Law et al. |
| 5,941,904 A | 8/1999 | Johnston et al. |
| 5,957,957 A | 9/1999 | Sheldon |
| 5,991,661 A | 11/1999 | Park et al. |
| 5,999,848 A | 12/1999 | Gord et al. |
| 5,999,849 A | 12/1999 | Gord et al. |
| 6,002,963 A | 12/1999 | Mouchawar et al. |
| 6,009,349 A | 12/1999 | Mouchawar et al. |
| 6,015,386 A | 1/2000 | Kensey et al. |
| 6,024,704 A | 2/2000 | Meador et al. |
| 6,032,699 A | 3/2000 | Cochran et al. |
| 6,033,398 A | 3/2000 | Farley et al. |
| 6,038,480 A | 3/2000 | Hrdlicka et al. |
| 6,044,297 A | 3/2000 | Sheldon et al. |
| 6,044,299 A | 3/2000 | Nilsson |
| 6,058,329 A | 5/2000 | Salo et al. |
| 6,061,593 A | 5/2000 | Fischell et al. |
| 6,077,136 A | 6/2000 | Arai et al. |
| 6,078,830 A | 6/2000 | Levin et al. |
| 6,081,748 A | 6/2000 | Struble et al. |
| 6,115,626 A | 9/2000 | Whayne et al. |
| 6,115,636 A | 9/2000 | Ryan |
| 6,120,442 A | 9/2000 | Hickey |
| 6,155,267 A | 12/2000 | Nelson |
| 6,163,716 A | 12/2000 | Edwards et al. |
| 6,163,725 A | 12/2000 | Peckham et al. |
| 6,165,135 A | 12/2000 | Neff |
| 6,171,252 B1 | 1/2001 | Roberts |
| 6,197,021 B1 | 3/2001 | Panescu et al. |
| 6,197,677 B1 | 3/2001 | Lee et al. |
| 6,206,835 B1 | 3/2001 | Spillman, Jr. et al. |
| 6,206,874 B1 | 3/2001 | Ubby et al. |
| 6,223,080 B1 | 4/2001 | Thompson |
| 6,234,973 B1 | 5/2001 | Meador et al. |
| 6,264,606 B1 | 7/2001 | Ekwall et al. |
| 6,277,078 B1 | 8/2001 | Porat et al. |
| 6,287,256 B1 | 9/2001 | Park et al. |
| 6,299,582 B1 | 10/2001 | Brockway et al. |
| 6,301,500 B1 | 10/2001 | Van Herk et al. |
| 6,309,350 B1 | 10/2001 | VanTassel et al. |
| 6,309,385 B1 | 10/2001 | Simpson |
| 6,328,699 B1 | 12/2001 | Eigler et al. |
| 6,360,123 B1 | 3/2002 | Kimchi et al. |
| 6,363,279 B1 | 3/2002 | Ben-Haim et al. |
| 6,366,811 B1 | 4/2002 | Carlson |
| 6,370,431 B1 | 4/2002 | Stoop et al. |
| 6,406,677 B1 | 6/2002 | Carter et al. |
| 6,418,348 B1 | 7/2002 | Witte |
| 6,421,567 B1 | 7/2002 | Witte |
| 6,438,408 B1 | 8/2002 | Mulligan et al. |
| 6,466,820 B1 | 10/2002 | Juran et al. |
| 6,473,638 B2 | 10/2002 | Ferek-Petric |
| 6,473,653 B1 | 10/2002 | Schallhorn et al. |
| 6,477,395 B2 | 11/2002 | Schulman et al. |
| 6,477,417 B1 | 11/2002 | Levine |
| 6,484,727 B1 | 11/2002 | Vaska et al. |
| 6,496,730 B1 | 12/2002 | Juran et al. |
| 6,580,946 B2 | 6/2003 | Struble |
| 6,584,362 B1 | 6/2003 | Scheiner et al. |
| 6,600,954 B2 | 7/2003 | Cohen et al. |
| 6,611,714 B1 | 8/2003 | Mo |
| 6,625,493 B2 | 9/2003 | Kroll et al. |
| 6,628,989 B1 | 9/2003 | Penner et al. |
| 6,666,826 B2 | 12/2003 | Salo et al. |
| 6,812,796 B2 | 11/2004 | Pryanishnikov et al. |
| 6,885,889 B2 | 4/2005 | Chinchoy |
| 6,934,584 B1 | 8/2005 | Wong et al. |
| 6,978,184 B1 | 12/2005 | Marcus et al. |
| 6,993,384 B2 | 1/2006 | Bradley et al. |
| 6,994,676 B2 | 2/2006 | Mulligan et al. |
| 7,020,523 B1 * | 3/2006 | Lu et al. .................... 607/27 |
| 7,047,084 B2 | 5/2006 | Erickson et al. |
| 7,174,218 B1 | 2/2007 | Kuzma |
| 7,200,437 B1 | 4/2007 | Nabutovsky et al. |
| 7,200,439 B2 | 4/2007 | Zdeblick et al. |
| 7,204,798 B2 | 4/2007 | Zdeblick et al. |
| 7,214,189 B2 | 5/2007 | Zdeblick et al. |
| 7,228,174 B2 * | 6/2007 | Burnes et al. .................... 607/17 |
| 7,267,649 B2 | 9/2007 | Zdeblick et al. |
| 7,467,016 B2 | 12/2008 | Colborn |
| 2001/0000187 A1 | 4/2001 | Peckham et al. |
| 2001/0002924 A1 | 6/2001 | Tajima |
| 2001/0025192 A1 | 9/2001 | Gerber et al. |
| 2001/0047138 A1 | 11/2001 | Kokate et al. |
| 2001/0053882 A1 | 12/2001 | Haddock et al. |
| 2002/0026183 A1 | 2/2002 | Simpson |

| | | |
|---|---|---|
| 2002/0040236 A1 | 4/2002 | Lau et al. |
| 2002/0045921 A1 | 4/2002 | Wolinsky et al. |
| 2002/0077568 A1 | 6/2002 | Haddock |
| 2002/0077673 A1 | 6/2002 | Penner et al. |
| 2002/0095196 A1 | 7/2002 | Linberg |
| 2002/0099419 A1 | 7/2002 | Cohen et al. |
| 2002/0111560 A1 | 8/2002 | Kokate et al. |
| 2002/0120186 A1 | 8/2002 | Keimel |
| 2002/0151816 A1 | 10/2002 | Rich et al. |
| 2002/0156417 A1 | 10/2002 | Rich et al. |
| 2002/0161307 A1 | 10/2002 | Yu et al. |
| 2002/0169445 A1 | 11/2002 | Jain et al. |
| 2002/0193859 A1 | 12/2002 | Schulman et al. |
| 2003/0078623 A1 | 4/2003 | Weinberg et al. |
| 2003/0100925 A1 | 5/2003 | Pape et al. |
| 2003/0105496 A1 | 6/2003 | Yu et al. |
| 2003/0153952 A1 | 8/2003 | Auricchio et al. |
| 2003/0191502 A1 | 10/2003 | Sharma et al. |
| 2004/0024440 A1 | 2/2004 | Cole |
| 2004/0039417 A1 | 2/2004 | Soykan et al. |
| 2004/0093053 A1 | 5/2004 | Gerber et al. |
| 2004/0097965 A1 | 5/2004 | Gardeski et al. |
| 2004/0098074 A1 | 5/2004 | Erickson et al. |
| 2004/0143154 A1 | 7/2004 | Lau et al. |
| 2004/0193021 A1 | 9/2004 | Zdeblick et al. |
| 2004/0199235 A1 | 10/2004 | Younis |
| 2004/0215049 A1 | 10/2004 | Zdeblick et al. |
| 2004/0220637 A1 | 11/2004 | Zdeblick et al. |
| 2004/0254483 A1 | 12/2004 | Zdeblick et al. |
| 2004/0260346 A1 | 12/2004 | Overall et al. |
| 2005/0027320 A1 | 2/2005 | Nehls et al. |
| 2005/0054892 A1 | 3/2005 | Lau et al. |
| 2005/0102011 A1 | 5/2005 | Lau et al. |
| 2005/0246004 A1 | 11/2005 | Cameron et al. |
| 2005/0267542 A1 | 12/2005 | David et al. |
| 2006/0058588 A1 | 3/2006 | Zdeblick |
| 2006/0122678 A1 | 6/2006 | Olsen et al. |
| 2006/0161211 A1 | 7/2006 | Thompson et al. |
| 2006/0247539 A1 | 11/2006 | Schugt et al. |
| 2006/0265038 A1 | 11/2006 | Hagen et al. |
| 2007/0100399 A1 | 5/2007 | Parramon et al. |
| 2007/0123944 A1 | 5/2007 | Zdeblick |
| 2007/0172896 A1 | 7/2007 | Goueli et al. |
| 2007/0179569 A1 | 8/2007 | Zdeblick |
| 2007/0198066 A1 | 8/2007 | Greenberg et al. |
| 2007/0203517 A1 | 8/2007 | Williams et al. |
| 2007/0219591 A1 | 9/2007 | Zdeblick et al. |
| 2007/0219608 A1 | 9/2007 | Swoyer et al. |
| 2007/0255336 A1 | 11/2007 | Herbert et al. |
| 2007/0255373 A1 | 11/2007 | Metzler et al. |
| 2007/0255460 A1 | 11/2007 | Lopata |
| 2008/0007186 A1 | 1/2008 | Lu et al. |
| 2008/0021292 A1 | 1/2008 | Stypulkowski |
| 2008/0027289 A1 | 1/2008 | Zdeblick |
| 2008/0039916 A1 | 2/2008 | Colliou et al. |
| 2008/0045826 A1 | 2/2008 | Greenberg et al. |
| 2008/0058656 A1 | 3/2008 | Costello et al. |
| 2008/0061630 A1 | 3/2008 | Andreu et al. |
| 2008/0091246 A1 | 4/2008 | Carey et al. |
| 2008/0097227 A1 | 4/2008 | Zdeblick et al. |
| 2008/0097566 A1 | 4/2008 | Colliou |
| 2008/0114230 A1 | 5/2008 | Addis |
| 2008/0140141 A1 | 6/2008 | Ben-David et al. |
| 2008/0140167 A1 | 6/2008 | Hagen et al. |
| 2008/0147168 A1 | 6/2008 | Ransbury et al. |
| 2008/0167702 A1 | 7/2008 | Ransbury et al. |
| 2008/0177343 A1 | 7/2008 | Dal Molin et al. |
| 2008/0255647 A1 | 10/2008 | Jensen et al. |
| 2008/0294062 A1 | 11/2008 | Rapoport et al. |
| 2008/0294218 A1 | 11/2008 | Savage et al. |
| 2008/0306394 A1 | 12/2008 | Zdeblick et al. |
| 2009/0024184 A1 | 1/2009 | Sun et al. |
| 2009/0054946 A1 | 2/2009 | Sommer et al. |
| 2009/0054947 A1 | 2/2009 | Bourn et al. |

FOREIGN PATENT DOCUMENTS

| | | |
|---|---|---|
| EP | 1048321 | 11/2000 |
| EP | 1050265 | 11/2000 |
| EP | 1136033 | 9/2001 |
| EP | 1266606 | 12/2002 |
| EP | 1321097 | 6/2003 |
| EP | 1426079 | 6/2004 |
| EP | 1938861 | 7/2008 |
| FR | 2097337 | 2/1972 |
| JP | 6456031 | 2/1988 |
| JP | 2-99036 | 4/1990 |
| JP | 3-055032 | 3/1991 |
| JP | 5269136 | 10/1993 |
| JP | 6501177 | 2/1994 |
| JP | 6-506619 | 4/1994 |
| JP | 7-542 | 1/1995 |
| JP | 2000139833 | 5/2000 |
| JP | 2000350705 | 12/2000 |
| JP | 2002272758 | 9/2002 |
| WO | WO9952588 | 10/1999 |
| WO | 01/43821 | 6/2001 |
| WO | WO0195787 | 12/2001 |
| WO | WO02053228 | 7/2002 |
| WO | WO02065894 | 8/2002 |
| WO | WO2004020040 | 3/2004 |
| WO | 2004/052182 | 6/2004 |
| WO | WO2004052182 | 6/2004 |
| WO | 2004/066814 | 8/2004 |
| WO | 2004/066817 | 8/2004 |
| WO | 2004/067081 | 8/2004 |
| WO | WO2004067081 | 8/2004 |
| WO | 2006/029090 | 3/2006 |
| WO | WO2006029090 | 3/2006 |
| WO | 2006/042039 | 4/2006 |
| WO | 2006/069322 | 6/2006 |
| WO | WO2006073915 | 7/2006 |
| WO | WO2006105474 | 10/2006 |
| WO | WO2007005641 | 1/2007 |
| WO | WO2007075974 | 7/2007 |
| WO | WO2007120884 | 10/2007 |
| WO | WO2007149546 | 12/2007 |
| WO | WO2008004010 | 1/2008 |
| WO | WO2008008755 | 1/2008 |
| WO | WO2008027639 | 3/2008 |

OTHER PUBLICATIONS

Borky et al., "Integrated Signal Conditioning for Silicon Pressure Sensors" IEEE Transactions on Electron Devices ED-26(12): 1906-1910 (1979).

Kovacs et al., "Technology Development for a Chronic Neutral Interface" A dissertation, Stanford University Aug. 1990 (1990) pp. 9, 225-257, 276.

Little et al, "The Output of the Heart and its Control" Physiology of the Heart and Circulation, 4th ed. 1989 Year Book Medical Publishers Inc. pp. 165-187.

Paolocci et al., "Positive inotropic and lusitropic effects of HNO/NO in failing hearts: Independence from β-adrenergic signaling" PNAS vol. 100, No. 9 (2003) 5537-5542.

Receveur et al., "Latteraly Moving Bi-Stable MEMS DC-Switch for Biomedical Applications" Medtronic Bakken Research Center, The Netherlands (2004) pp. 854-856.

U.S. Appl. No. 11/917,992, filed Jul. 13, 2009; Jensen et al., (2009) "Deployable Epicardial Electrode and Sensor Array" 69pp.

U.S. Appl. No. 12/097,959, filed Nov. 17, 2008; Zdeblick et al., (2008) "Implantable Integrated Circuit" 199pp.

U.S. Appl. No. 12/395,538, filed Feb. 27, 2009; Bi et al., (2009) "Integrated Circuit Implementation and Fault Control System, Device, and Method" 163pp.

* cited by examiner

AUTOMATED OPTIMIZATION OF MULTI-ELECTRODE PACING FOR CARDIAC RESYNCHRONIZATION

CROSS-REFERENCE TO RELATED APPLICATIONS

Pursuant to 35 U.S.C. §119 (e), this application claims priority to the filing dates of: U.S. Provisional Patent Application Ser. No. 60/667,575 filed Mar. 31, 2005; U.S. Provisional Patent Application Ser. No. 60/667,529 filed Mar. 31, 2005; U.S. Provisional Patent Application Ser. No. 60/684,751 filed May 25, 2005; and U.S. Provisional Patent Application Ser. No. 60/695,577 filed Jun. 29, 2005; the disclosures of which are herein incorporated by reference.

BACKGROUND

1. Field of the Invention

The present invention relates to monitoring and administering electric signals in living tissues. In particular, the present invention relates to a method and system for automatically optimizing multi-electrode pacing for cardiac resynchronization therapies.

2. Related Art

Cardiac resynchronization therapy (CRT) is an important new medical intervention for patients suffering from congestive heart failure. In congestive heart failure, symptoms develop due to the inability of the heart to function sufficiently well as a mechanical pump to supply blood to meet the body's physiological needs. Congestive heart failure is typically characterized by a gradual decline in cardiac function, punctuated by severe exacerbations leading eventually to death. Over five million patients in the United States are estimated to suffer from this malady.

The aim of cardiac resynchronization pacing is to induce the interventricular septum and the left ventricular free wall to contract at approximately the same time. Resynchronization therapy seeks to provide a contraction time sequence that can most effectively produce maximal cardiac output with minimal total energy expenditure by the heart. Generally, the optimal timing may be calculated by reference to hemodynamic parameters such as dP/dt, the first-order time derivative of the pressure waveform in the left ventricle. The dP/dt parameter is a well-documented proxy for left ventricular contractility.

In current practice, external ultrasound measurements are used to calculate the dP/dt parameter. An external ultrasound is used to observe wall motion directly. A clinician uses the ultrasound system in a tissue Doppler mode, which provides a feature known as tissue Doppler imaging (TDI), to evaluate the time course of displacement of the septum relative to the left ventricle free wall. Ultrasonographic evaluation using TDI or a similar approach can be an important tool for qualifying patients for CRT.

CRT as currently delivered is effective in about half to two-thirds of patients implanted with a resynchronization device. In approximately one third of these patients, CRT provides a two-class improvement in patient symptoms as measured based on the New York Heart Association (NYHA) fair level scale. In another one third, a one-class improvement in cardiovascular symptoms can be accomplished. In the remaining third, there is no improvement or, in a small minority, even a deterioration in cardiac performance. This third group of patients is referred to as non-responders. Furthermore, the NYHA one-class responders may experience only marginal or partial improvements, given the unfavorable results seen in the minority.

The synchronization therapy, in order to be optimal, targets the point of maximal delay on a cardiac wall segment, and advances the timing thereof to synchronize contraction with an earlier contracting region of the heart, such as the septum. The current placement technique for CRT devices is mostly empirical. A physician typically cannulates a vein that appears to be in the region described by the literature as most effective. He can then position the pacing device and perform stimulation. The lack of extra cardiac stimulation, such as diaphragmatic pacing, is confirmed. The current available techniques rarely provide sufficient time or means for optimizing the cardiac resynchronization process.

In general, CRT optimization must be performed through a laborious manual method performed by an ultrasonographer evaluating cardiac wall motion at different lead positions and different interventricular delay (IVD) settings. IVD refers to the difference between the timing of pacing pulses sent to different locations, such as the right ventricle and left ventricle. Pace makers can vary the atrio-ventricular delay, which is the delay between stimulations sent to the atria and the ventricle or ventricles. These timing settings are important in addition to the location of the pacing electrode in the left ventricle.

Some research efforts to assess cardiac motion through internal sensors have been made in the past. U.S. Pat. No. 6,625,493, entitled "Orientation of Patient's Position Sensor Using External Field," to Kroll et al., filed on Aug. 24, 2001, discloses a positional accelerometer for indicating a patient's vertical acceleration. U.S. Pat. No. 6,002,963, entitled "Multi-Axial Accelerometer-Based Sensor for an Implantable Medical Device and Method of Measuring Motion Measurements There from," to Mouchawar et al., filed on Feb. 17, 1995, discloses cardiac wall motion detection using an accelerometer. U.S. Pat. No. 5,991,661, entitled "System and Method for Measuring Cardiac Activity," to Park et al., filed on Oct. 17, 1997, discloses the use of an accelerometer for rate-adaptive pacing. U.S. Pat. No. 6,044,299, entitled "Implantable Medical Device Having an Accelerometer," to Nilsson, filed on Sep. 19, 1997, discloses an in-can accelerometer for providing rate control.

In addition to incorporating sensors in a pacing lead, a pacing lead can accommodate multiple pacing electrodes to provide flexibility in selecting pacing locations. U.S. Pat. No. 6,473,653, entitled "Selective Activation of Electrodes within an Implantable Lead," to Schallhorn et al., filed on Mar. 2, 2000, discloses an implantable multi-electrode lead adapted to allow selective activation of the included electrodes to electrically excite the tissue in the vicinities of the activated electrodes. The Schallhorn system requires a controller for each electrode, and separate conductors for sending analog excitation pulses configuration commands to these controllers. Consequently, these controller circuits and conductors make the Schallhorn system bulky and unsuitable for many size-sensitive applications. U.S. Pat. No. 5,593,430, entitled "Bus System for Interconnecting an Implantable Medical Device with a Plurality of Sensors," to Renger, filed on Jan. 27, 1995, discloses a two-conductor bus system for connecting physiologic sensors to a pacemaker. The two-conductor bus provides power to the sensors, and the sensors' output signals are modulated on the two wires.

With the flexibility of a multi-electrode lead comes the difficulty in selecting the optimal electrode and timing configurations, because the number of possible configurations increases geometrically with the number of available electrodes. Currently, TDI is the common technique for characterizing dyssynchrony with accuracy. TDI measures myocardial movement throughout the cardiac cycle and can quantify the timing differences between peak tissue movements in multiple areas of the left ventricle, which suggest the presence of dyssynchrony. TDI can also be used to determine cardiac wall positions via external ultrasonography, typically for purposes of measuring valve function, cardiac output, or rarely, synchrony index. However, TDI is a complex manual procedure and hence is time consuming and labor intensive. There are currently no clinically useful techniques for determining optimal CRT configurations on a substantially automatic or a real-time, machine-readable basis.

Hence, a need arises for a method for automated optimization of multi-electrode pacing for cardiac resynchronization.

SUMMARY

One embodiment of the present invention provides a system for automatically optimizing CRT procedures using a multi-electrode pacing lead. During operation, the system performs a first set of iterations to select one or more satellites on one or more pacing leads inserted in a patient. A pacing lead includes a plurality of pacing satellites, and a pacing satellite includes a plurality of electrodes that can be individually addressed and used for transmitting or detecting electric signals. The system then performs a second set of iterations to select one or more electrodes on the selected satellites. The system further performs a third set of iterations to select one or more timing configurations for pacing signals transmitted through one or more of the selected electrodes.

A further embodiment of the present invention provides a graphic user interface (GUI) for configuring a cardiac pacing lead that accommodates a plurality of pacing satellites. The GUI provides an illustration of the pacing lead, which indicates the status of a plurality of electrodes on each pacing satellite. The GUI also provides a selection field that allows a user to configure a polarity, rate, amplitude, and pulse width of a pacing signal that is to be transmitted to the pacing lead.

The present invention has important clinical applications in improving results from cardiac resynchronization therapy (CRT). The dP/dt parameter is a well-documented proxy for left ventricular contractility. Use of the present invention allows optimization of CRT as evaluated by the dP/dt parameter by about 5-50%, more specifically from about 10-20%, and most specifically by about 15%. Similar improvements can also be seen using changes in responder claims, cardiac output, and synchrony index measures.

DETAILED DESCRIPTION

Figure 1:
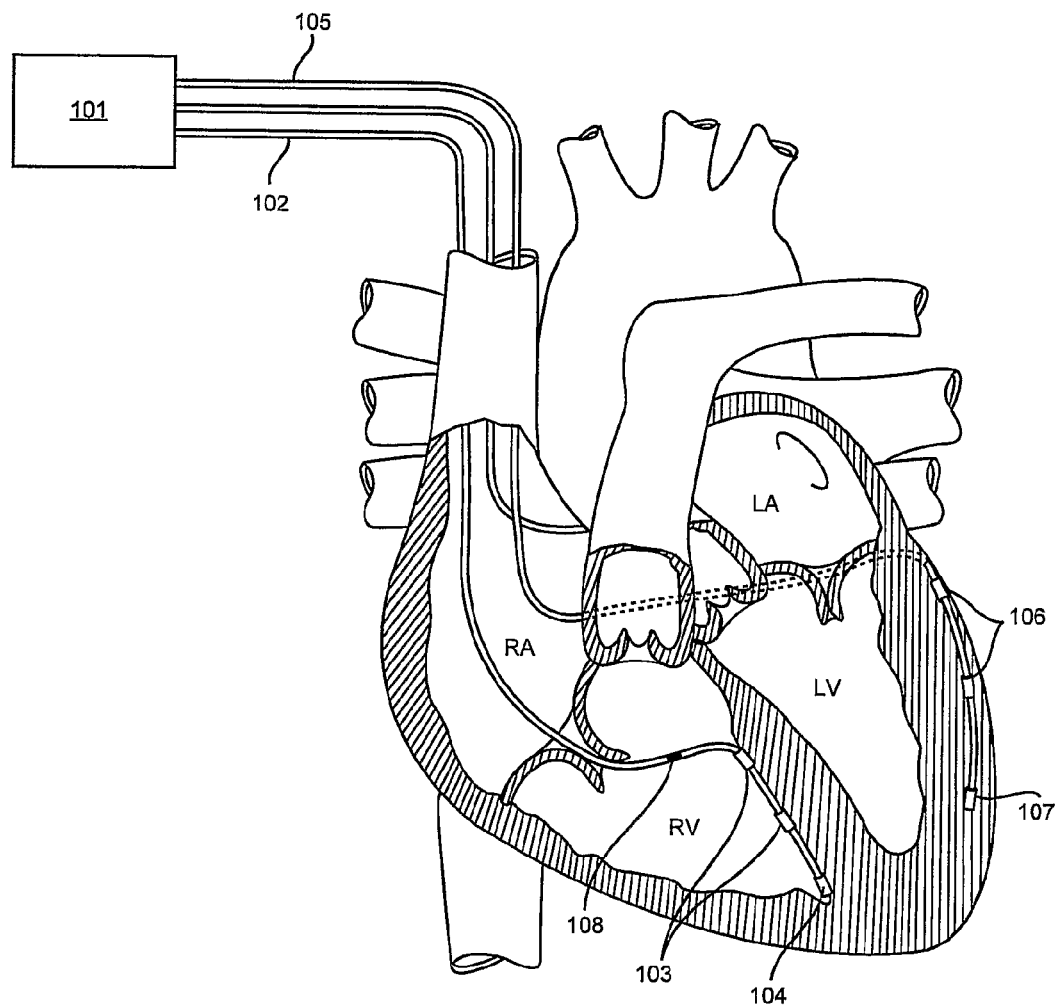
FIG. 1 illustrates the locations of a number of pacing satellites incorporated in a multi-electrode pacing lead, in accordance with an embodiment of the present invention.

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

The data structures and the programs for performing operations described in this detailed description are typically stored on a computer readable storage medium, which may be any device or medium that can store code and/or data for use by a computer system. This includes, but is not limited to, application specific integrated circuits (ASICs), field-programmable gate arrays (FPGAs), semiconductor memories, magnetic and optical storage devices such as disk drives, magnetic tape, CDs (compact discs), and DVDs (digital versatile discs or digital video discs).

Embodiments of the present invention provide a system that automatically optimizes the configuration of a multi-electrode pacing lead for cardiac pacing and for detecting signals from sensors incorporated on the lead. According to one embodiment, a pacing lead includes a number of pacing circuit elements, referred to as "satellites," which further include a number of electrodes. Each satellite and the electrodes therein can be individually addressed and controlled through a low-power control chip. The satellites are coupled to a pacing-control system, which can be a pacing can or an external control system. One embodiment of such a multi-electrode pacing lead is described in a prior application by some of the present inventors.

A multi-electrode pacing lead can contain a number of satellites, each of which containing multiple electrodes. A large number of combinations are therefore possible for transmitting bi-polar or uni-polar (when, for example, the pacing can is used as signal return) pacing signals. Furthermore, identifyiing the optimal timing delay between two pacing signals sent to two locations can involve hundreds or thousands of trial data points, because the delay between heartbeats is on the order of one second, and the cardiac synchrony is measured on the order of milliseconds. The number of possible timing configurations, when multiplied by the number of possible satellite/electrode combinations, can make the cost of optimization prohibitively high. For example, in a bi-ventricular pacemaker system with at least one lead having eight satellites where each satellite has four electrodes, a clinician can face billions of configurations with different satellite/electrode/timing combinations. Using TDI to scan manually through all possible configurations is impossible. Without an automated optimization process, the clinician can only experiment with a small number of configurations. Such an empirical approach is not optimally reliable or effective.

Embodiments of the present invention provide a system that can quickly identify valid satellite and electrode combinations by performing hierarchical iterations. The system then uses a directed search to find optimized timing configuration for each electrode combination. The system subsequently detects peaks of the best synchrony and provides the corresponding satellite/electrode and timing configurations to the physician. If the identified configurations are unacceptable, the system can further indicate that a change of lead placement may be necessary.

Multi-Electrode Pacing Lead

FIG. 1 illustrates the locations of a number of pacing satellites incorporated in a multi-electrode pacing lead, in accordance with an embodiment of the present invention. A pacing and signal detection system 101 provides extra-cardiac communication and control elements for the overall system. In some embodiments, pacing and signal detection system 101 may be, for example, a pacing can of a pacemaker residing in an external or extra-corporeal location.

Right ventricular lead 102 emerges from pacing and signal detection system 101 and travels from a subcutaneous location from pacing and signal detection system 101 into the patient's body (e.g., preferably, a subclavian venous access), and through the superior vena cava into the right atrium. From the right atrium, right ventricle lead 102 is threaded through the tricuspid valve to a location along the walls of the right ventricle. The distal portion of right ventricular lead 102 is preferably located along the intra-ventricular septum, terminating with a fixation in the right ventricular apex. Right ventricular lead 102 includes satellites positioned at locations 103 and 104. The number of satellites in ventricular lead 102 is not limited, and may be more or less than the number of satellites shown in FIG. 1.

Similarly, left ventricular lead 105 emerges from pacing and signal detection system 101, following substantially the same route as right ventricular lead 102 (e.g., through the subclavian venous access and the superior vena cava into the right atrium). In the right atrium, left ventricular lead 105 is threaded through the coronary sinus around the posterior wall of the heart in a cardiac vein draining into the coronary sinus. Left ventricular lead 105 is provided laterally along the walls of the left ventricle, which is likely to be an advantageous position for bi-ventricular pacing. FIG. 1 shows satellites positioned at locations 106 and 107 along left ventricular lead 105.

Right ventricular lead 102 may optionally be provided with pressure sensor 108 in the right ventricle. A signal multiplexing arrangement allows a lead to include such active devices (e.g., pressure sensor 108) for pacing and signal collection purposes (e.g., right ventricular lead 102). Pacing and signal detection system 101 communicates with each of the satellites at locations 103, 104, 106 and 107. The electrodes controlled by the satellites may also be used to detect cardiac depolarization signals. Additionally, other types of sensors, such as an accelerometer, strain gauge, angle gauge, temperature sensor, can be included in any of the leads.

Figure 2:
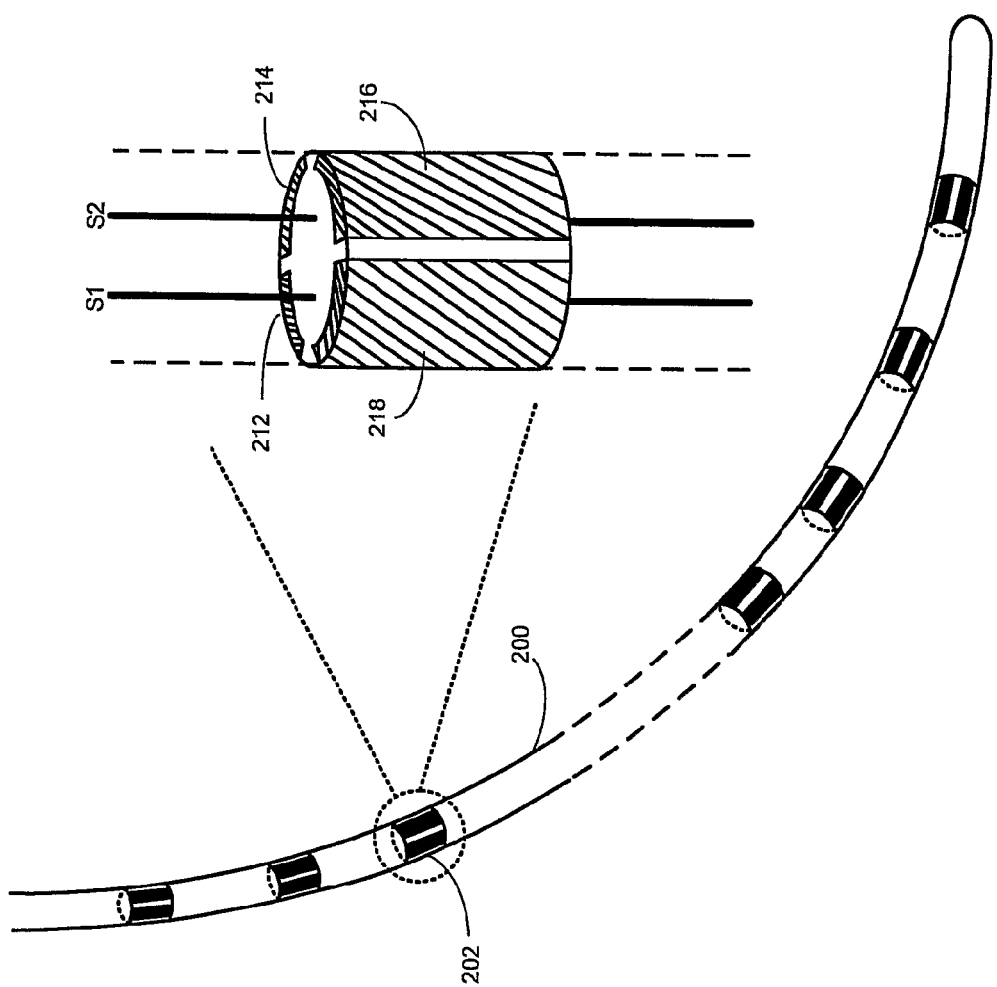
FIG. 2 illustrates an exemplary external view of a number of pacing satellites, in accordance with an embodiment of the present invention.

FIG. 2 illustrates an exemplary external view of a number of pacing satellites, in accordance with an embodiment of the present invention. According to one embodiment, a pacing lead 200 (e.g., right ventricular lead 102 or left ventricular lead 105 of FIG. 1) accommodates two bus wires S1 and S2, which are coupled to a number (e.g., eight) of satellites, such as satellite 202. FIG. 2 also shows satellite 202 with a zoom-in view. Satellite 202 includes electrodes 212, 214, 216, and 218, located in the four quadrants of the cylindrical outer walls of satellite 202. Each satellite also contains a control chip which communicates with a pacing and signal-detection system to receive configuration signals that determine which of the four electrodes are to be coupled to bus wires S1 or S2.

The configuration signals, the subsequent pacing pulse signals, and the analog signals collected by the electrodes can all be communicated through bus wires S1 and S2, in either direction. Since both digital and analog signals can be communicated through bus wires S1 and S2, no digital-to-analog or analog-to-digital converters need to be provided in the satellites. Although shown in a symmetrical arrangement, electrodes 212, 214, 216 and 218 may be offset along lead 200 to minimize capacitive coupling among these electrodes. The quadrant arrangement of electrodes allows administering pacing current via electrodes oriented at a preferred direction, for example, away from nerves, or facing an electrode configured to sink the pacing current. Such precise pacing allows low-power pacing and minimal tissue damage caused by the pacing signal.

Hierarchical Iterative Optimization

Since a multi-electrode lead can provide a large number of electrode combinations for pacing purposes, to identify effective combinations quickly is very advantageous. Theoretically, a system can automatically try every possible electrode combination and timing configuration in a brute-force manner, which is time consuming. Embodiments of the present invention employ three levels of hierarchical iterations to expedite the optimization process. With such a process, the system can quickly eliminate satellite and electrode combinations that cannot effectively produce a cardiac response.

For the purposes of this application, "valid" means an electrode satellite group which captures heart muscle, and in the case of a segmented electrode one which also avoids phrenic nerve capture. Also for the purposes of this application, "configure" means the timing and electrode selection provided-that is on-off and polarity selection.

Because the system aims to identify the valid satellite combinations, electrode combinations, and timing configurations, one approach is to conduct the trial pacing in three corresponding levels. That is, the system first experiments with all possible satellite combinations and identifies valid ones. Valid means pacing capture occurs and, at the segmented electrode selection level, phrenic nerve capture does not occur. Then, based on the valid satellite combinations, the system further experiments with all possible electrode combinations and identifies those that are valid. Finally, the system experiments with all possible timing configurations and identifies those that are optimal. This hierarchical iteration process can also be performed with a specified or limited scope of possible configurations. For example, a physician can specify certain satellites, electrodes, or timing configurations with which the system is to experiment. In general, this hierarchical iteration process can be used to perform both global and local optimization.

Figure 3:
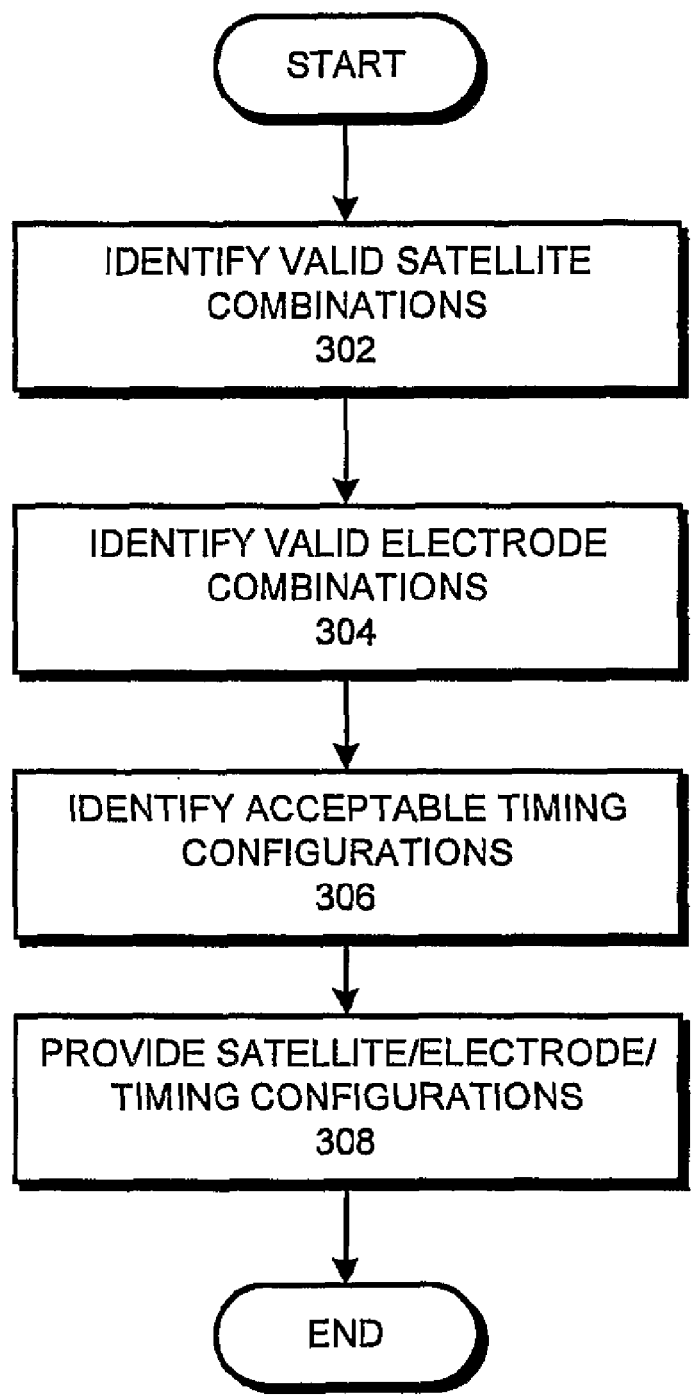
FIG. 3 presents a high-level flow chart illustrating the automated optimization process using hierarchical iterations, in accordance with an embodiment of the present invention.

FIG. 3 presents a high-level flow chart illustrating the automated optimization process using hierarchical iterations, in accordance with an embodiment of the present invention. During operation, the system first identifies the valid satellite combinations (step 302). The system then identifies the valid electrode combinations among electrodes on the valid satellites identified in step 302 (step 304). Next, the system identifies acceptable timing configurations using valid electrodes identified in step 304 (step 306). The system subsequently provides the optimal satellite/electrode/timing configurations to a physician (step 308).

During the first set of iterations, the system experiments with all satellite combinations. In one embodiment, the system uses all the electrodes on a satellite when pacing through that satellite. When performing the iterations, the system sequentially selects satellite pairs, wherein one satellite is used as signal source and another as signal sink for bipolar pacing. The system can also include uni-polar pacing in the iterations. In uni-polar pacing, the pacing can be used as signal source (or sink) and one satellite is used as signal sink (or source). The uni-polar pacing can be viewed as a special instance of bipolar pacing, wherein the can functions as a satellite with only one electrode. In one embodiment, the system performs $_{n+1}P_2$ iterations, where P denotes the permutation operation, n denotes the total number of satellites, and (n+1) indicates that the pacing can be considered as a satellite for uni-polar pacing. In a further embodiment, more than one satellite can be used as the signal source or signal sink.

During each iteration, the system transmits a pulse through the satellite pair. If the pulse results in a cardiac response, such as a contraction, the satellite pair is considered as a valid combination, which is saved. Otherwise, the system continues to experiment with the next untested satellite combination. The presence of valid satellite combinations may depend on lead placement. If the system does not identify any valid satellite combination, the system can indicate that a change of the lead placement may be considered.

Figure 4:
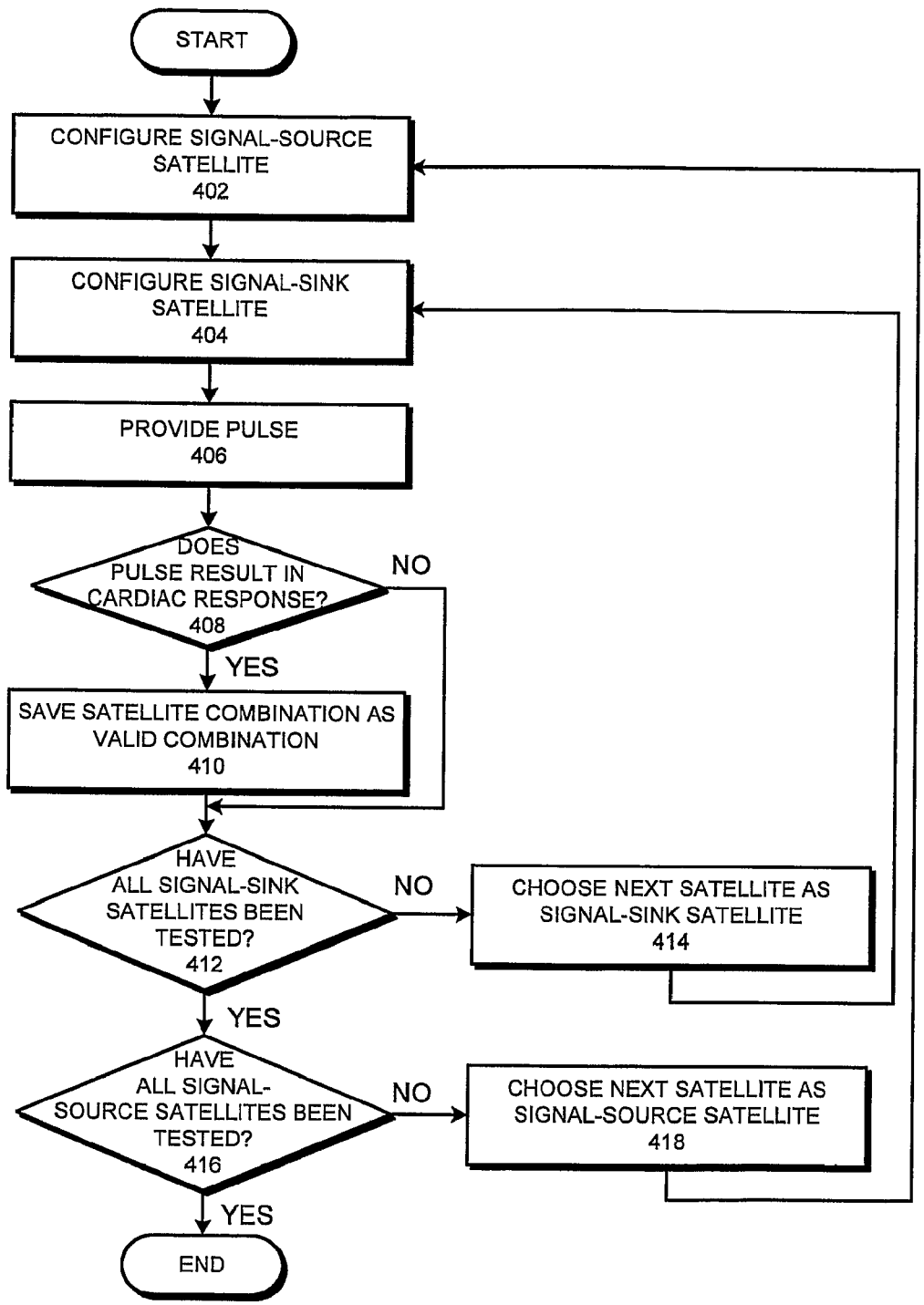
FIG. 4 presents a flow chart illustrating, in conjunction with step 302 of FIG. 3, an exemplary implementation of the process of identifying valid satellite combinations, in accordance to one embodiment of the present invention.

FIG. 4 presents a flow chart illustrating, in conjunction with step 302 of FIG. 3, an exemplary implementation of the process of identifying valid satellite combinations, in accordance to one embodiment of the present invention. During operation, the system first configures a signal-source satellite (step 402) and a signal-sink satellite (step 404). The system then provides a pacing pulse through the configured satellites (step 406), and determines whether the pulse results in a cardiac response (step 408).

If a response is present, the system saves the satellite combination as a valid combination (step 410). Otherwise, the system proceeds to determine whether all signal-sink satellites have been tested in combination with the current signal-source satellite (step 412). If not, the system chooses the next untested satellite as the signal-sink satellite (step 414) and configures this next satellite (step 404). If all signal-sink satellites have been tested, the system further determines whether all signal-source satellites have been tested (step 416). If not, the system chooses the next untested satellite as the signal-source satellite (step 418) and configures this next satellite (step 402). Otherwise, the system exits the current set of iterations for selecting valid satellite combinations.

After identifying valid satellite combinations, the system performs the second set of iterations to select valid electrode combinations from the electrodes on all the valid satellites. Thus, by eliminating satellite combinations that do not produce a cardiac response, the system also eliminates the associated electrode combinations. This elimination significantly reduces the search space for the second set of iterations.

Figure 5:
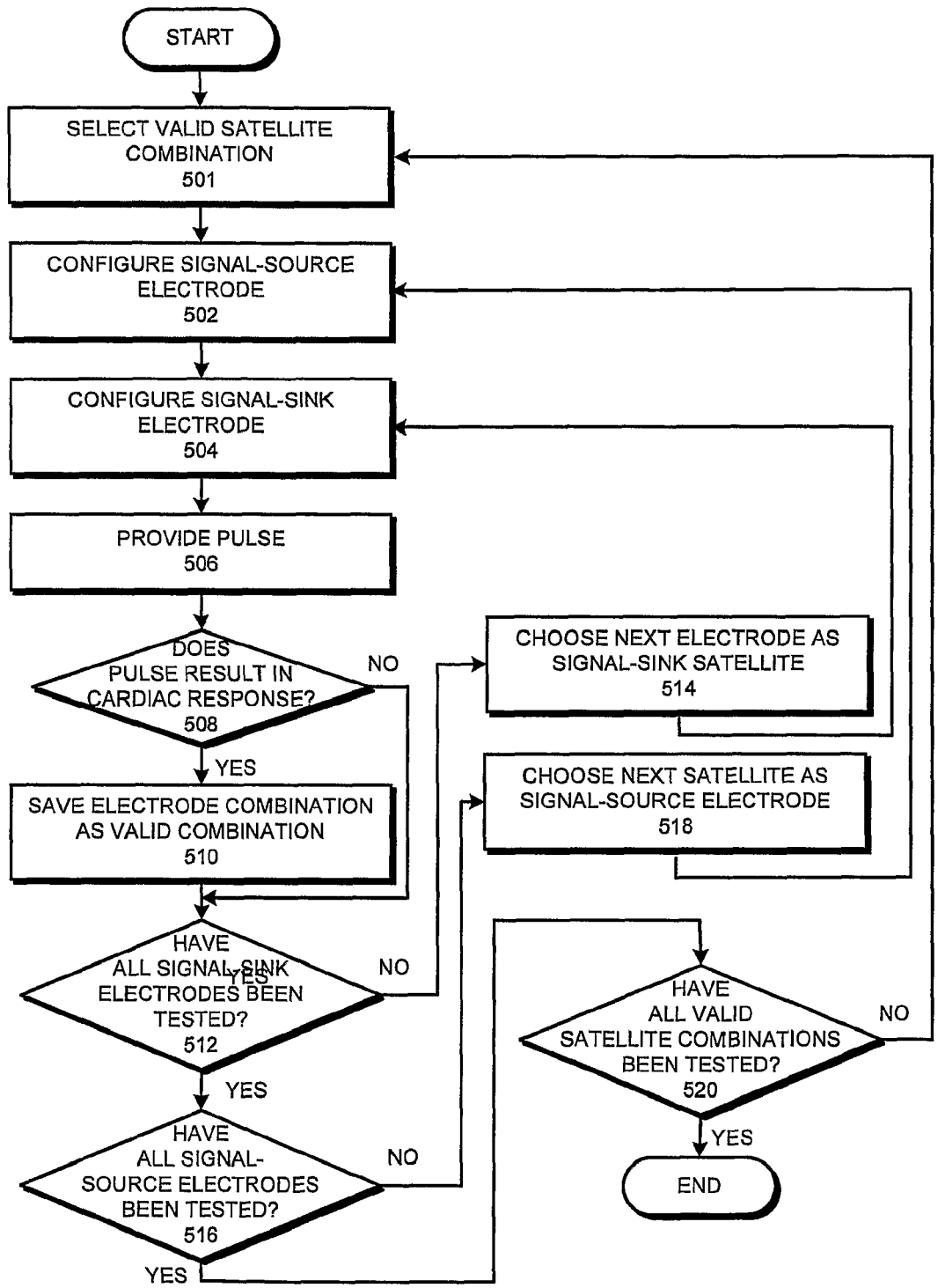
FIG. 5 presents a flow chart illustrating, in conjunction with step 304 of FIG. 3, an exemplary implementation of the process of identifying valid electrode combinations, in accordance with an embodiment of the present invention.

FIG. 5 presents a flow chart illustrating, in conjunction with step 304 of FIG. 3, an exemplary implementation of the process of identifying valid electrode combinations, in accordance with an embodiment of the present invention. During operation, the system first selects a valid satellite combination (step 501). The system then configures a signal-source electrode on the valid signal-source satellite (step 502) and a signal-sink electrode on the valid signal-sink satellite (step 504). The system subsequently provides a pacing pulse through the configured electrodes (step 506), and determines whether the pulse results in a cardiac response (step 508).

Some of the inventors' clinical testing indicates that pacing using one or two electrodes in a quadrant reduces the capture threshold voltage and increases the electrode impedance. This effect is in contrast to when all four quadrants are employed in a ring like manner. The capture threshold reduction ranges from about 20% to as much as 75%, more specifically from about 30%-60%, and most specifically about 50%. The impedance increase is in the range of 100% (1 vs. 4 electrodes)

This combination has a powerful effect on power consumed in the pacing function given P=i*i*R, lowering V, reducing current. Increasing R lowers current. Optimization may focus on finding the one or two optimal electrodes in a quadrant. The risk is the optimal electrode may shift until the lead fixates several weeks after implant.

If a response is present, the system saves the electrode combination as a valid combination (step 510). Otherwise, the system proceeds to determine whether all electrodes on the signal-sink satellite have been tested in combination with the current signal-source electrode (step 512). If not, the system chooses the next untested electrode on the signal-sink satellite as the signal-sink electrode (step 514) and configures this next electrode (step 504). If all signal-sink electrodes have been tested, the system further determines whether all electrodes on the signal-source satellite have been tested (step 516). If not, the system chooses the next untested electrode on the signal-source satellite as the signal-source electrode (step 518) and configures this next electrode (step 502). Otherwise, the system determines whether all valid satellite combinations have been tested (step 520). If not, the system proceeds to select the next valid satellite combination (step 501). Otherwise, the system exits the current set of iterations for selecting valid electrode combinations.

After identifying the valid satellite and electrode combinations, the system then enters the third set of iterations to identify optimal timing configurations. The goal is to find a timing configuration, which can be the time delay between two pacing signals or between one pacing signal and the contraction of a specific location, so that the heart can attain the best synchrony. Because the synchrony can be sensitive of a timing difference of only a few milliseconds while the period between two consecutive heartbeats is on the order of one second, hundreds or even over a thousand of test data points are present. By example, there can be about 100-10,000 test data points, more specifically about 500-1,000 test data points, and most specifically about 700 test data points. One approach to find the timing configuration with the best synchrony is to perform a brute-force, exhaustive search by experimenting with every possible timing configuration with a fixed step length, for example, 1 ms. This approach, however, can be very time consuming and may not be clinically practical.

One embodiment of the present invention employs two rounds of iteration for searching timing configurations that produce the best synchrony. In the first round of iterations, the system scans through all the valid electrode combinations, and, for each electrode combination, the system experiments with different timing configurations using a coarse-granularity step length, and records the measured corresponding synchrony. The term "electrode combination" here refers to a first valid electrode configured as a signal source and a second valid electrode configured as a signal sink, and hence includes different valid satellite combinations. Based on a synchrony-versus-delay plot, the system identifies broad peaks of best synchrony values using a given set of criteria. In the second round of iterations, the system focuses on and re-scans these broad peaks, and experiments with different timing configurations using a fine-granularity step length. The system can thereby quickly and accurately identify timing configurations that result in the best available synchrony.

This two-level iterative process can be analogized to the process of finding a target object under a microscope. A viewer first uses a low-power objective lens to scan the specimen and locates the approximate region where the target is. The user then places the target region in the center of the view field and changes to a high-power objective lens. By adjusting the focus and fine-tuning the position of the specimen, the user can quickly obtain a clear view of the target object. In the present system, the first round of iterations with a coarse-granularity step length resembles locating the target region with a low-power objective lens; and the second round of iterations with a fine-granularity step length resembles the focusing and fine-tuning with the high-power objective lens.

The ratio between the coarse-granularity and find-granularity step lengths can be set at a default value or be determined by a clinician. In one embodiment, the coarse-granularity step length is approximately about 5-10 times the fine-granularity step length. In a further embodiment, the coarse-granularity step length is about 5-10 ms. Most broadly, this step length can be between about 4-40 ms, more specifically from about 10-30 ms, and most specifically about 15 ms. By contrast, the fine-granularity step length is between about 0.05 and 4.00 ms, more specifically between about 0.10 and 2.00 ms, and most specifically about 1 ms. Other step-length ratios and values are also possible.

Figure 6:
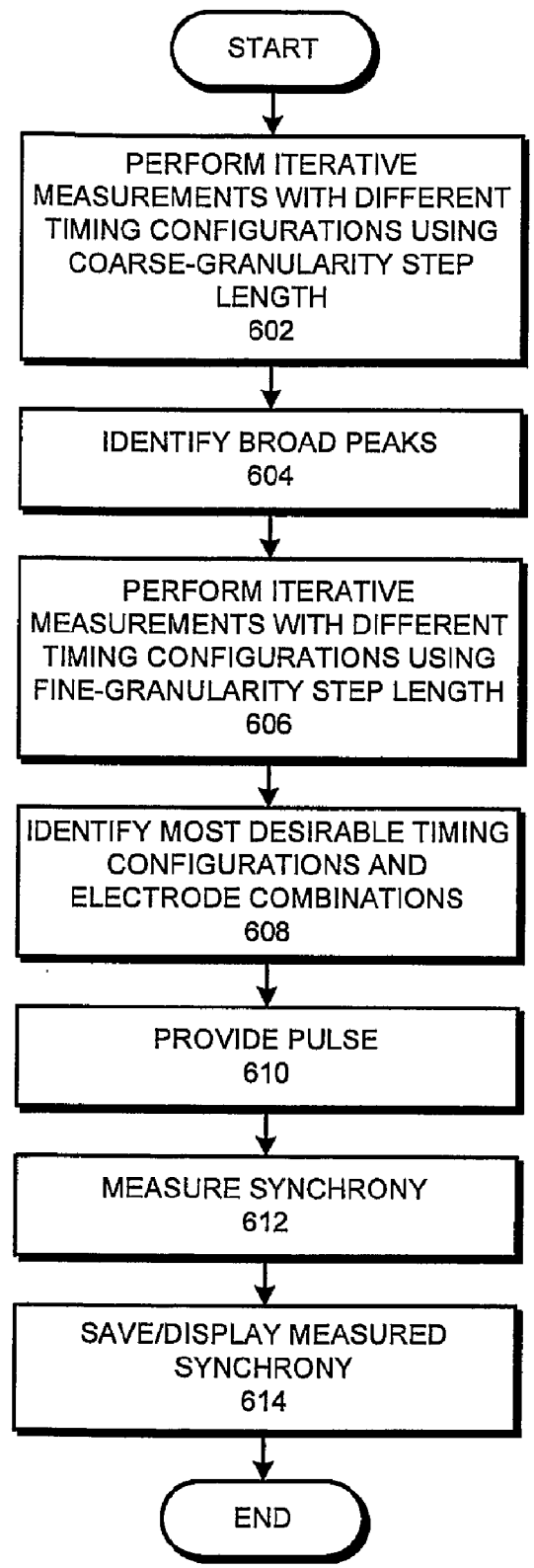
FIG. 6 presents a flow chart illustrating, in conjunction with step 306 of FIG. 3, an exemplary implementation of the process of identifying acceptable timing configurations, in accordance with an embodiment of the present invention.

FIG. 6 presents a flow chart illustrating, in conjunction with step 306 of FIG. 3 an exemplary implementation of the process of identifying acceptable timing configurations, in accordance with an embodiment of the present invention. During operation, the system performs a first round of iterative measurements of synchrony with different timing configurations for all the valid electrode combinations using a coarse-granularity step length (step 602). The system subsequently identifies broad peaks for synchrony (step 604).

Next, the system performs a second round of iterative measurements of synchrony with different timing configurations centered around the broad peaks, using a fine-granularity step length (step 606). The system then identifies the most desirable timing configuration(s) and the corresponding electrode combination(s) (step 608). The system subsequently provides a pulse through the optimal electrode combination with the optimal timing configuration (step 610), and measures the synchrony (step 612). The system further saves and displays the measured synchrony to a clinician (step 614).

Figure 7:
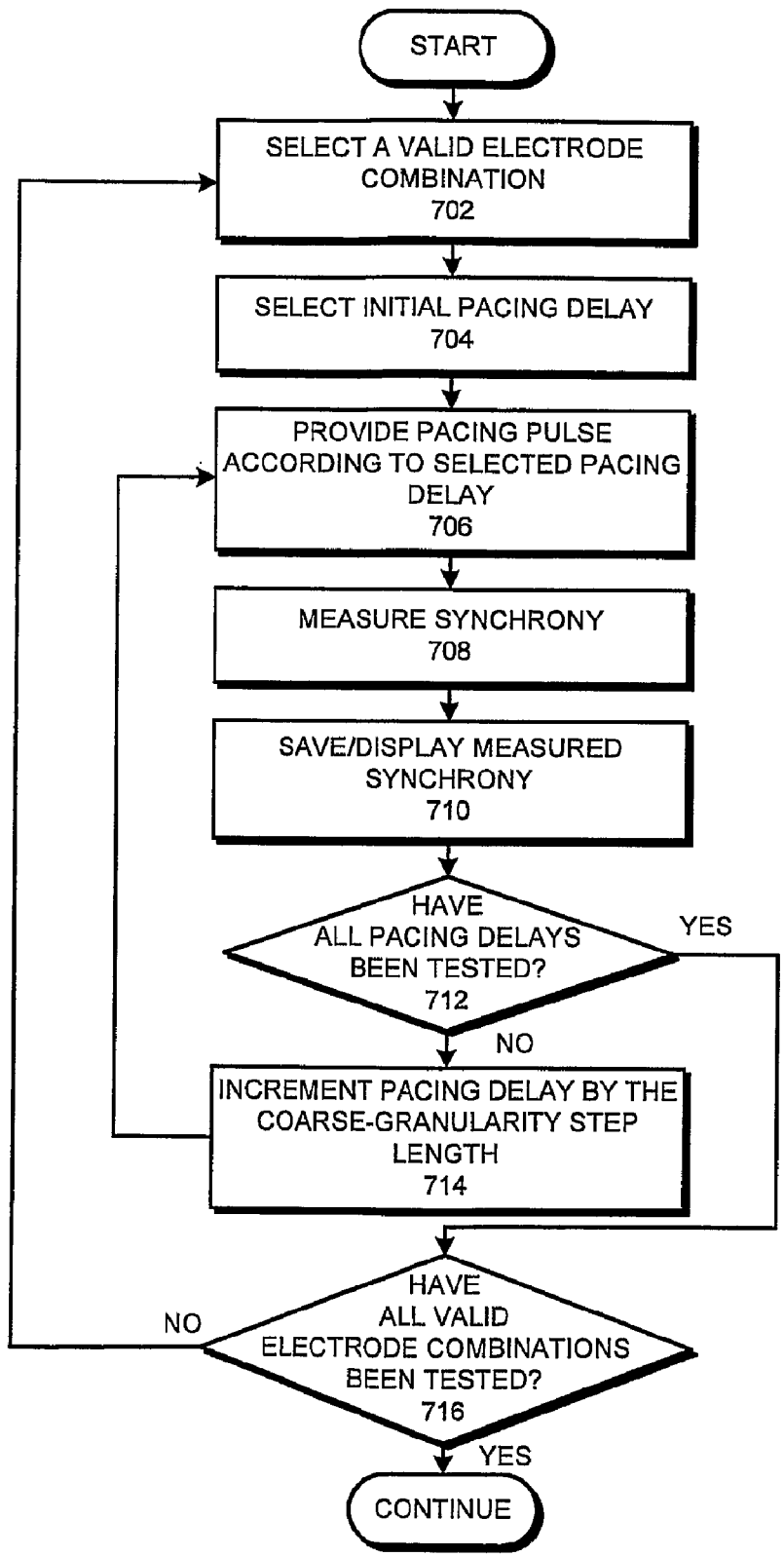
FIG. 7 presents a flow chart illustrating, in conjunction with step 602 of FIG. 6, an exemplary implementation of the process of performing iterative measurements with different timing configurations using a coarse-granularity step length, in accordance with an embodiment of the present invention.

FIG. 7 presents, a flow chart illustrating, in conjunction with step 602 of FIG. 6, an exemplary implementation of the process of performing iterative measurements with different timing configurations using a coarse-granularity step length, in accordance with an embodiment of the present invention. The system selects a valid electrode combination (step 702), and selects an initial pacing delay (step 704). The system then provides pacing pulse according to the selected pacing delay through the selected electrodes (step 706). Next, the system measures synchrony (step 708), saves and displays the measured synchrony (step 710).

The system subsequently determines whether all pacing delays have been tested (step 712). If not, the system increments the pacing delay by the coarse-granularity step length (714) and provides another pacing pulse with the new pacing delay (step 706). If all pacing delays have been tested, the system further determines whether all valid electrode combinations have been tested (step 716). If not, the system selects the next valid electrode combination (step 702) and performs the iterations again. Otherwise, the system exits.

After the first round of iterations, the system identifies the broad peaks of synchrony. In one embodiment, the system plots synchrony versus pacing delay for every valid electrode combination, thereby creating a number of two-dimensional plottings. On each plotting, the system can first identify the peaks, which are data points with the highest synchrony indices. The system then expands the peak to include a number of neighboring data points, for example 100 data points, on both sides of the peak. These data points define the width a corresponding broad peak, which is subsequently used for locating the highest-synchrony. In one embodiment, data points immediately adjacent to a data point with the same or a higher synchrony are eliminated, since such data points are part of the same broad peak. The system can further trace paths for the remaining data points. If the derivative of the path between two data points does not show a sign change, then the data points are identified as being part of the same broad peak.

In a further embodiment, the width of each broad peak is determined by a pre-determined cut-off synchrony value, which can be set at a percentage of the synchrony value of the peak point. For example, the cut-off value can be between about 20% and 90%, more specifically between 35% and 66%, and most specifically about 50% of the peak synchrony value.

In yet a further embodiment, the system compares two identified peaks by first multiplying each peak's height with the peak's width at a cut-off threshold, and then comparing the corresponding products. This product can be referred to as a cross sectional area. The peaks with the largest cross sectional areas or a cross sectional area above a threshold is identified as a broad peak.

The system can also visually display a synchrony map, which indicates the synchrony with different timing and electrode configurations. A clinician can then visually identify the synchrony peaks. In one embodiment, the clinician selects a peak that is displayed on a computer screen using a mouse, trackball, touch-screen, or joystick.

Figure 8:
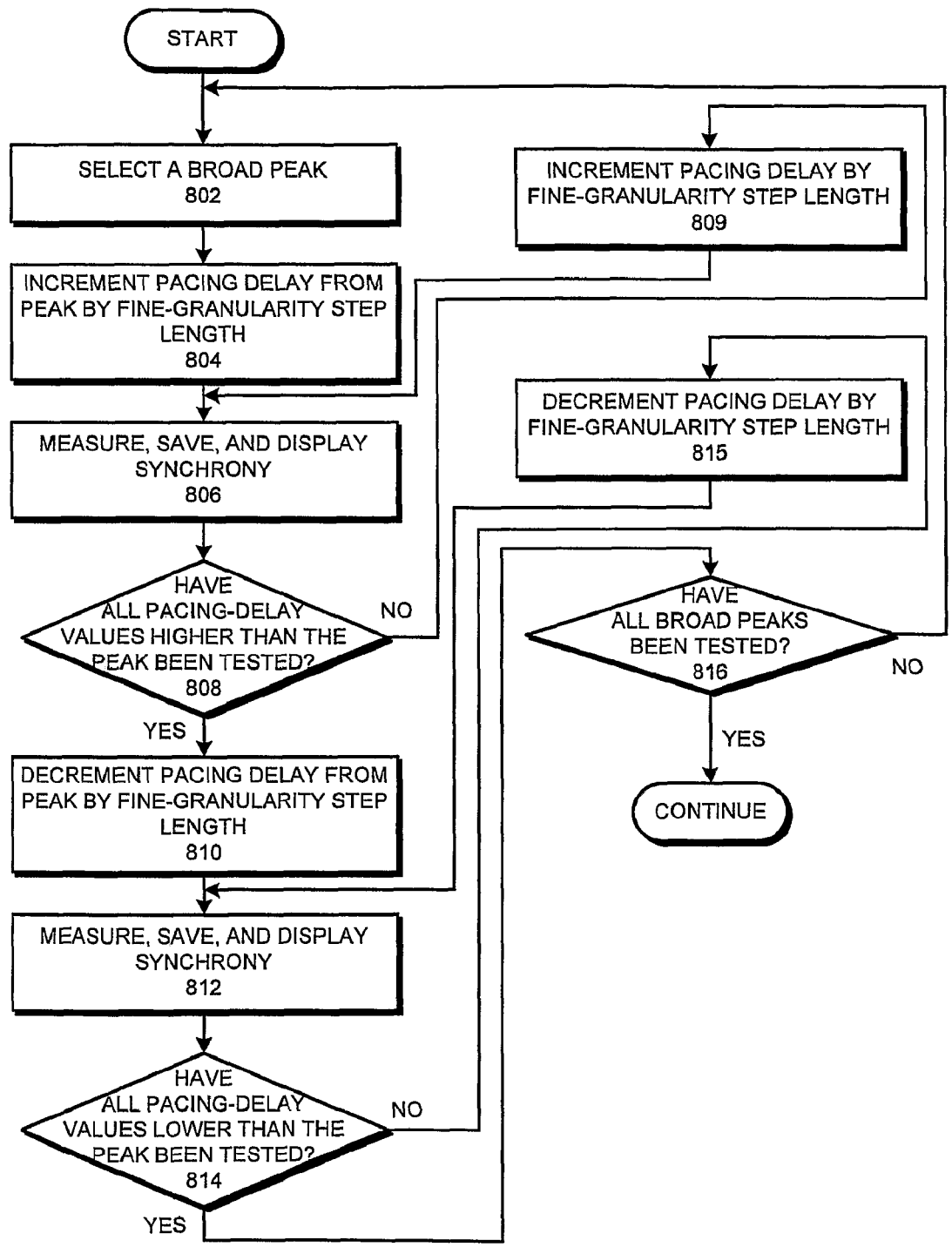
FIG. 8 presents a flow chart illustrating, in conjunction with step 606 of FIG. 6, an exemplary implementation of the process of performing iterative measurements with different timing configurations using a fine-granularity step length, in accordance with an embodiment of the present invention.

FIG. 8 presents a flow chart illustrating, in conjunction with step 606 of FIG. 6, an exemplary implementation of the process of performing iterative measurements with different timing configurations using a fine-granularity step length, in accordance with an embodiment of the present invention. The system first selects a synchrony broad peak (step 802), and increments the pacing delay from the value corresponding to the peak by the fine-granularity step length (step 804). The system then measures, saves, and displays the synchrony (step 806). The system further determines whether all pacing-delay values higher than the value corresponding to the peak have been tested (step 808). If not, the system increments the pacing delay by the fine-granularity step length (step 809) and continues to measure the new synchrony (step 806).

If all pacing-delay values higher than the value corresponding to the peak value have been tested, the system then decrements the pacing delay from the value corresponding to the peak by the fine-granularity step length (step 810). The system measures, saves, and displays the synchrony (step 812), and determines whether all pacing-delay values lower than the value corresponding to the peak have been tested (step 814). If not, the system continues to decrement pacing delay by the fine-granularity step length (step 815) and measures the new synchrony (step 812).

If all pacing-delay values lower than the value corresponding to the peak have been tested, the system further determines whether all the broad peaks have been tested (step 816). If not, the system continues to select the next broad peak and repeats the iterative process (step 802). Otherwise, the system exits.

Automated Optimization Using Scripting

Typically, the system uses different hardware and middleware modules to control the multi-electrode pacing lead. To perform the automated optimization process, these modules are driven with different parameters in a given sequence, while response data are collected simultaneously. One possible approach to implement such a system is to develop customized, embedded software tailored to specific hardware used in the system. Such a system, however, can be costly and inflexible, because the control software is closely coupled to the underlying hardware and middleware, and cannot be easily modified.

One embodiment of the present invention uses a scripting language to control the hardware and middleware. A scripting language, compared with other types of programming languages, are usually simpler to learn and use, and does not need to be complied. The scripting language is interpreted by a computer at run-time, so that the machine can execute instructions immediately. Using a scripting language allows the present system to de-couple the underlying middleware that drives the hardware, from the high-level logical controls. For example, the system can include a first middleware module that configures the multi-electrode lead and provides pacing pulses with different timing configurations, and a second module that collects sensor response signals. The system can then perform the automated optimization process using a script program that controls these middleware modules to carry out the hierarchical iterations described above.

Using scripting language has many advantages. Scripting effectively de-couples the logical programming from the underlying hardware and middleware. Such de-coupling makes the present system modular and allows each hardware or middleware module to be used for more than one application. Scripting also provides a wide range of flexibility and allows a user to reconfigure parameters for the optimization easily. With a graphic scripting tool, one can create specific scripts by manipulating (e.g., drag and drop) graphic objects and by inputting numerical or alphabetical values. Such a tool is particularly useful to clinicians who are not familiar with coding computer programs. For example, a clinician can use the graphic scripting tool to create a special test sequence, which may or may not involve the aforementioned hierarchical iterations, to experiment with a specific set of electrode/timing configurations. The graphic scripting tool can generate a corresponding script to perform the test sequence.

Another advantage of using scripting language is that a user can save and load test data with great flexibility. A script can specify the format in which the system saves data. The system can also allow a user to load previously saved data obtained for a specific patient at a specific time. Furthermore, a script can manage additional complex data processing tools to perform various manipulations on the collected data.

In one embodiment, the present system includes a configuration and driver module and a data collection module, which are based on LabVIEW-compatible hardware from National Instruments Inc. of Austin, Tex.

Synchrony Measurement

Embodiments of the present invention provide a number of ways for measuring and displaying synchrony information. The various ways of displaying synchrony described herein allow a clinician to observe synchrony in real-time and in an intuitive manner. Additionally, the input of the clinician can assist with the optimization process in, for example, choosing the broad peaks.

Figure 9:
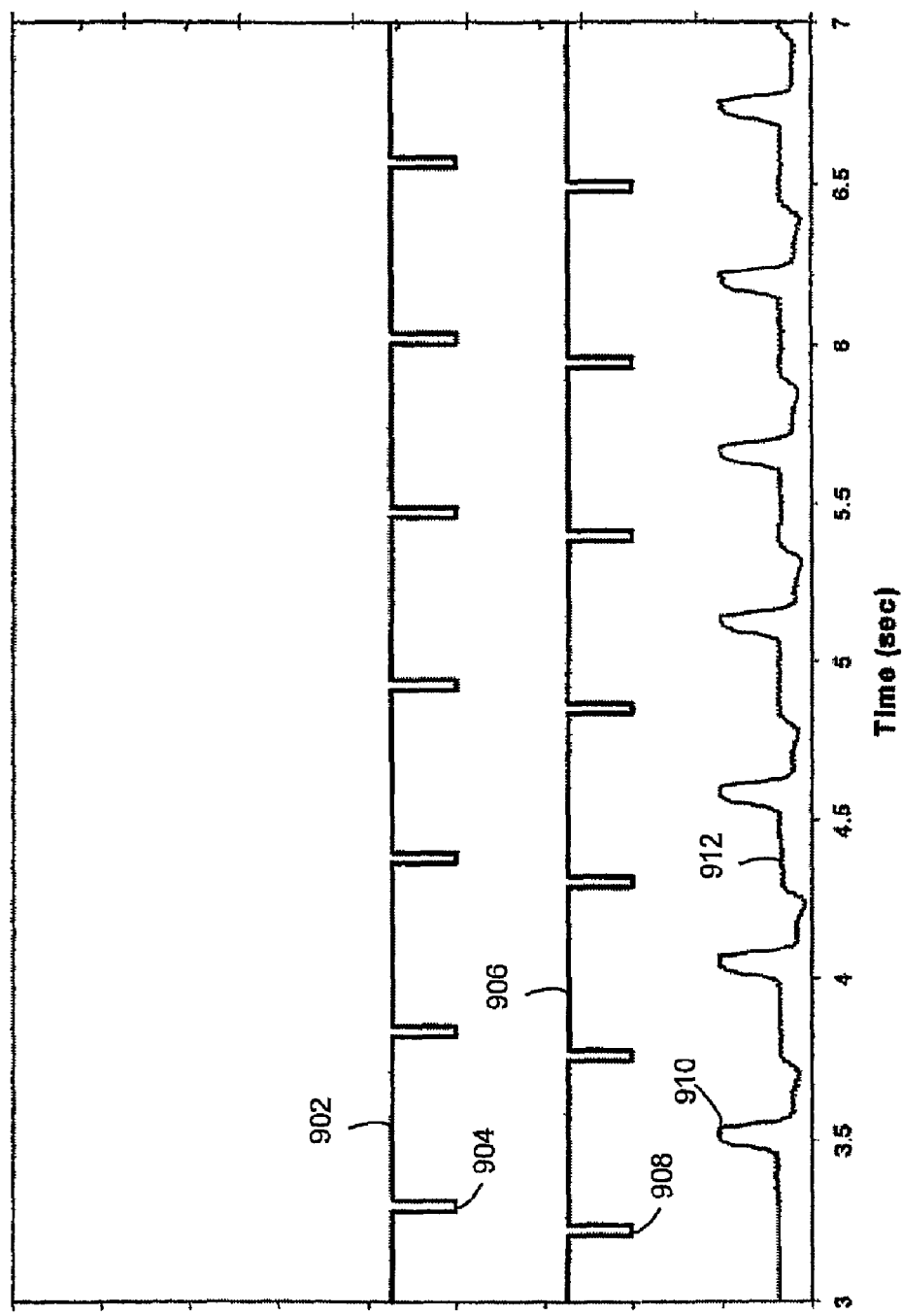
FIG. 9 illustrates an electrocardiogram (ECG) signal, measured in a pig's heart, in response to a right-ventricle pacing signal and a left-ventricle packing signal, in accordance to an embodiment of the present invention.

Typically, the synchrony is measured as the timing difference between two sensor signals in response to the pacing signals. FIG. 9 illustrates an electrocardiogram (ECG) signal, measured in a pig's heart, in response to a right-ventricle pacing signal and a left-ventricle packing signal, in accordance to an embodiment of the present invention. The pacing signals include a left-ventricle signal 902 and a right-ventricle signal 906, both of which provide negative pulses. A right-ventricle pulse 908 is followed by a left-ventricle pulse 904, which is further followed by a peak 910 of an ECG signal 912. The timing difference between pulses 904 and 908 constitutes a specific timing configuration. The system measures the synchrony as a function of the pulse-timing differences.

Synchrony measurement typically involves measuring the timing difference between corresponding characteristic points of two sensor signals, which indicate cardiac contractions at two different locations. Embodiments of the present invention allow the system to use relative values, instead of absolute values, of sensor signals for measuring synchrony. Relative values are based on signals from an uncalibrated sensor. The system can thereby avoid calibration of these sensors, which can be time consuming and expensive, because the size, location, and signal drifting of the sensors can make calibration very difficult. Furthermore, using relative and dimensionless values reduces the processing required for conversion or normalization. Consequently, the response time for synchrony measurement can be reduced, which in turn expedites the optimization process. In further embodiments, the system may normalize or weight the sensor signals before measuring the synchrony.

Furthermore, embodiments of the present invention can tolerate signal drift without using a filter, because signal drift does not significantly change the position of a peak. Nevertheless, an optional low frequency filter can be used to remove drift. For example, the heart beats at a frequency of approximately 1 Hz. The measured sensor signals therefore also have a frequency of about 1 Hz. A typical drift is on the order of 0.1 to 0.2 Hz. A high-pass filter may have a cut-off frequency from about 0.05 to 0.2 Hz, more specifically between 0.10 and 0.15 Hz, and most specifically at about 0.1 Hz can be used to remove the drift.

Figure 10:
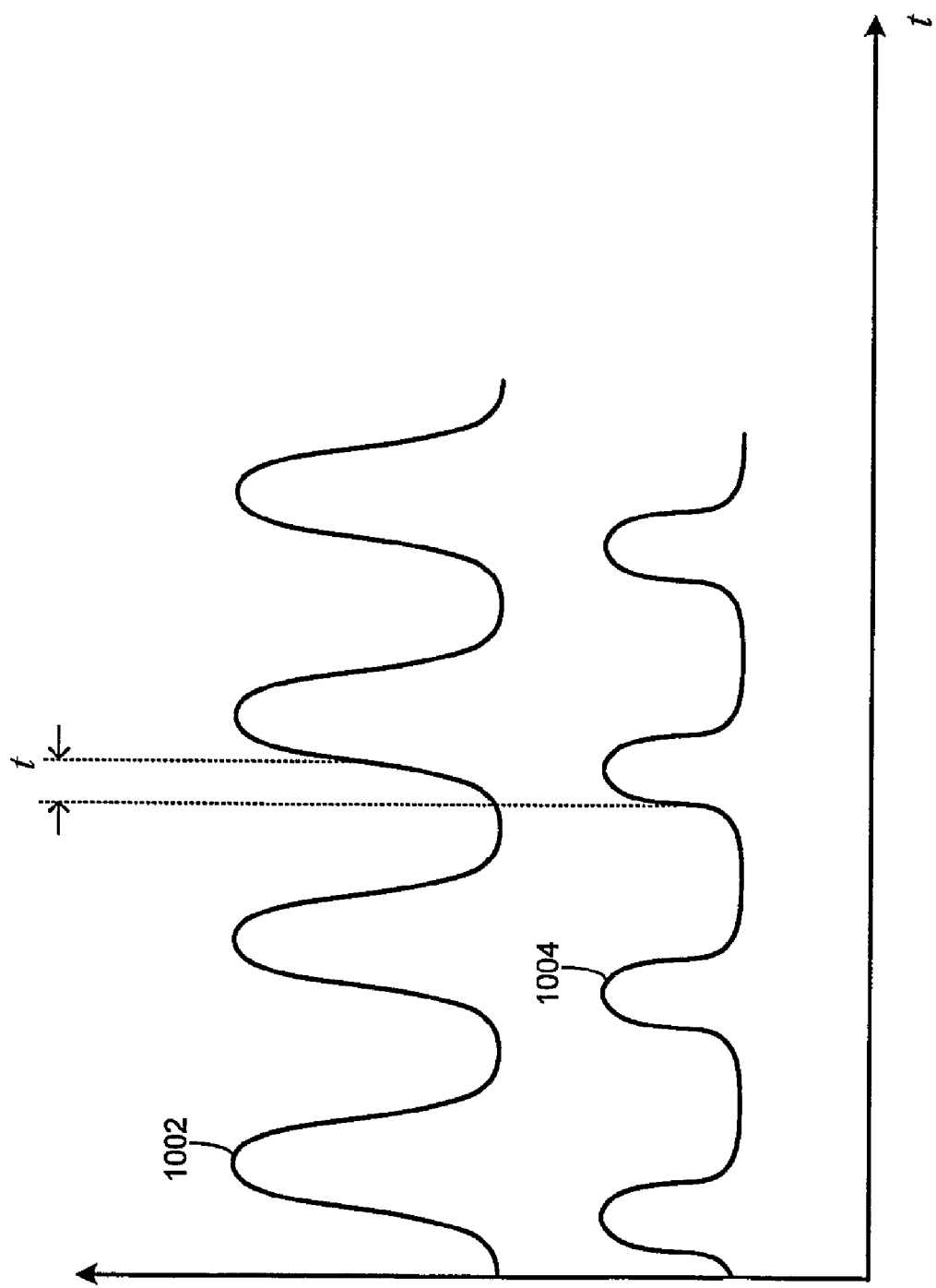
FIG. 10 illustrates measuring the timing difference between two cardiac signals using their corresponding relative values, in accordance with an embodiment of the present invention.

FIG. 10 illustrates measuring the timing difference between two cardiac signals using their corresponding relative values, in accordance with an embodiment of the present invention. A strain gauge in the left ventricle generates a signal 1002, and a second sensor in the right ventricle generates a signal 1004. The characteristic points chosen for comparison are the maximum-slew-rate points of the two signals. Slew rate is the rate of change (or slope) of a signal. The maximum slew rate point of a signal is where the signal changes at the highest rate.

The system determines the synchrony by measuring the timing difference, $\Delta t$, between the maximum-slew-rate points of the two signals. In one embodiment, the system calculates a synchrony index based on the absolute value of $\Delta t$. A better synchrony is attained with a smaller absolute value of $\Delta t$. The system can further group the measured synchrony into three groups, namely "good," "OK," and "bad," based on two thresholds x and y. If $\Delta t < x$, then the synchrony is designated as "good." If $x < \Delta t < y$, the synchrony is designated as "OK." If $\Delta t > y$, the synchrony is designated as "bad."

In a further embodiment, the system can calculate $|\Delta t_T - \Delta t|$, the absolute value of the difference between $\Delta t$ and a target time delay $\Delta t_T$. The optimal synchrony corresponds to the smallest absolute value of the difference. In a preferred embodiment, the target time delay is zero.

Further embodiments of the present invention can employ time-average operations to smooth the sensor signals and to eliminate interferences due to noises and distortions. The system can automatically configure a time window for averaging the signals based on the instant rate of change of the signal. If the instant rate of change is high and the sign of the signal slope varies frequently, the signal may experience heavy noise and interferences, and the system can use a larger averaging time window. The system can also allow a user to specify the averaging time window. Although performing time averaging to the signal precludes a real-time measurement of the synchrony, doing so can make the measurements more accurate.

In a further embodiment, the system computes a cross-correlation between the two sensor signals. Computing the cross-correlation allows use of the entire signal, instead of just one point, to measure synchrony. Doing so helps reduce errors caused by noise, interferences, or distortions, which may be due to harmonics. For example, the system can compute a cross-correlation function based on left-ventricle signal 1002 and right-ventricle signal 1004. The cross-correlation of two sampled (time-discrete) signals can be computed as:

$$r = \frac{\sum x - \overline{x} \cdot y - \overline{y}}{\sqrt{[\sum (x - \overline{x})^2] \cdot [\sum (x - \overline{x})^2]}}$$

wherein x and y are the amplitude of the two signals, respectively, and wherein $-1 \leq r \leq 1$ is the cross-correlation coefficient. When the cross-correlation coefficient $r=1$, a complete positive correlation is present between the two signals. That is, the signals are in phase, and the best synchrony is attained. When $r=-1$, there is complete negative correlation between the signals, and the signals are completely out of phase. The value of r indicates the degree to which the correlation lies between full synchrony and complete negative synchrony. When $r=0$, the signals are considered uncorrelated.

In one embodiment, the system applies thresholds, x and y, to determine the quality of the synchrony. If $r \geq x$, then the synchrony is designated as "good." If $x > r \geq y$, the synchrony is designated as "OK." If $y > r$, the synchrony is designated as "bad." In a further embodiment, thresholds may designate results in a range bounded on both sides of zero as "good," values adjacent to either side of the range as "OK," and values further away from either side of the rage as "bad."

Because the system allows use of relative, or dimensionless, values signals from different types of sensors can be used to measure synchrony. For example, the two signals shown in FIG. 10 can be from a strain gauge and an accelerometer, respectively. In general, any sensors capable of indicating cardiac contraction can be used for synchrony measurements. Such sensors include, but are not limited to, angle gauges, strain gauges, pressure sensors, electropotential sensors, volume flow sensors, piezoelectric sensors, and accelerometers. Furthermore, a sensor can be incorporated on a signal chip which is included in the lead.

Synchrony Display

Embodiments of the present invention employ a number of ways to display or indicate synchrony information, so that a clinician can observe the response signals and assist with the optimization process.

Figure 11:
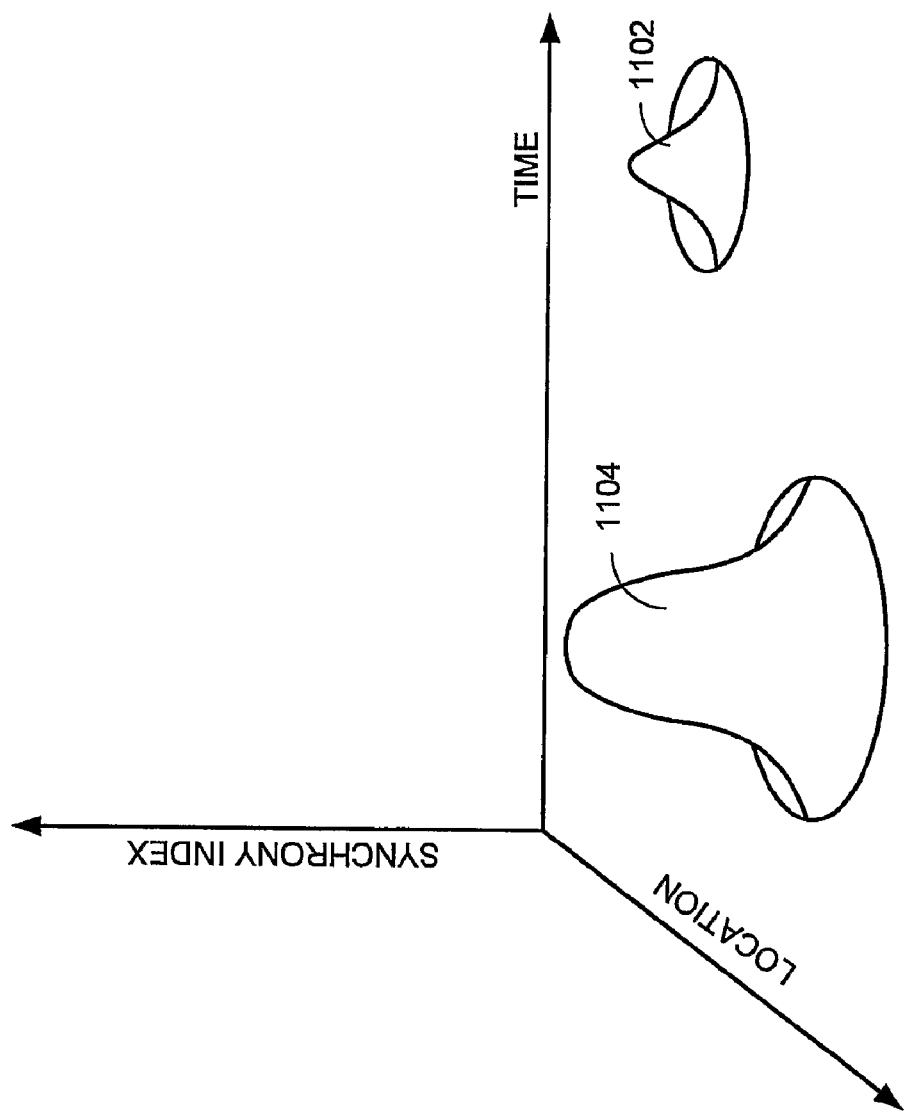
FIG. 11 is an exemplary illustration of a three-dimensional plot of synchrony indices versus the timing delay between two pacing pulses and the locations of the pacing electrodes, in accordance with an embodiment of the present invention.

FIG. 11 is an exemplary illustration of a three-dimensional plot of synchrony indices versus the timing delay between two pacing pulses and the locations of the pacing electrodes, in accordance with an embodiment of the present invention. The X-axis of the display indicates the timing delay between two pacing signals, one of which is transmitted to the left ventricle, and the other to the right ventricle. In this example, one of the pacing electrodes is fixed, and the location of the other one is varied by selecting different electrodes on a multi-electrode lead. The Y-axis indicates the location of the varying electrode. The Z-axis indicates a synchrony index, which can be a cross-correlation coefficient between signals from two sensors placed in the two ventricles. The display illustrates two three-dimensional peaks, 1102 and 1104. Peak 1102 is lower than peak 1104. The system may select peak 1104 as the broad peak, because peak 1102 is too low or too narrow.

Figure 12:
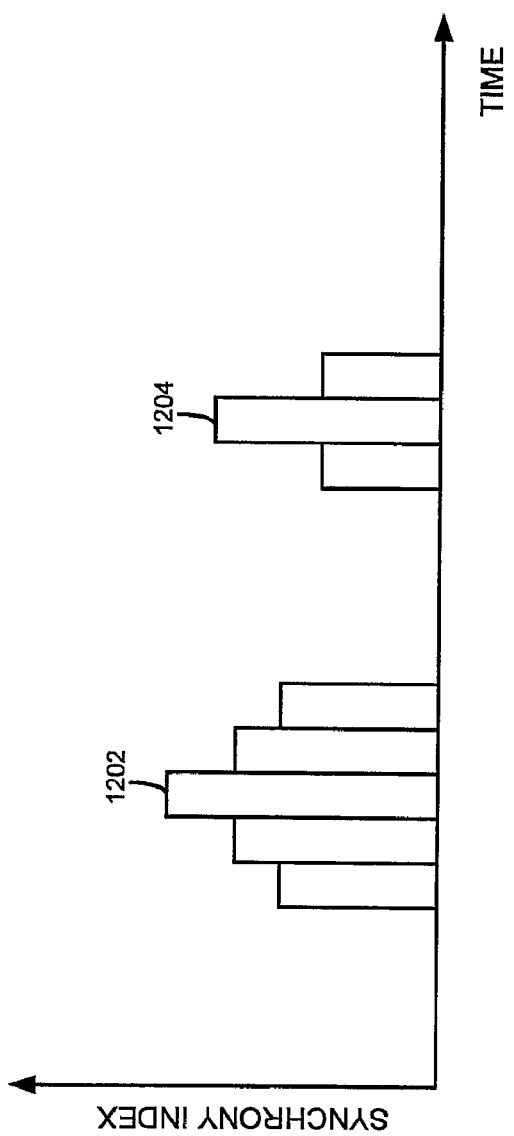
FIG. 12 is an exemplary illustration of a two-dimensional plot of a synchrony index versus the timing delay between two pacing pulses, in accordance with an embodiment of the present invention.

FIG. 12 is an exemplary illustration of a two-dimensional plot of a synchrony index versus the timing delay between two pacing pulses, in accordance with an embodiment of the present invention. The X-axis indicates the timing delay between two pacing signals, one of which is transmitted to the left ventricle, and the other to the right ventricle. The Y-axis indicates a synchrony index. Note that this two-dimensional display only plots different synchrony-index values at different timing configurations with a given electrode combination. Such a two-dimensional display can be considered as one of the possible cross-sections of a three-dimensional display as illustrated in FIG. 11. The two-dimensional display illustrates two peaks, 1202 and 1204. Peak 1204 is lower than peak 1202. The system may select peak 1202 as the broad peak, because peak 1204 is too low or too narrow.

Figure 13:
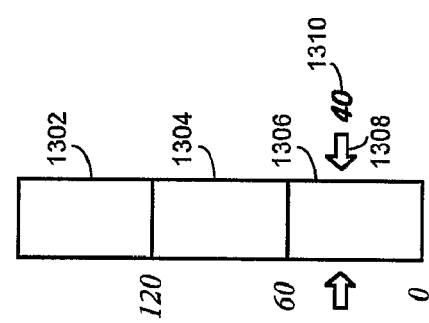
FIG. 13 is an exemplary illustration of a linear display for synchrony index, in accordance with an embodiment of the present invention.

FIG. 13 is an exemplary illustration of a linear display for synchrony index, in accordance with an embodiment of the present invention. This display indicates the timing delay between the corresponding points of two signals by changing the position of an indicator 1308 along a vertical bar. The vertical bar includes three regions, 1302, 1304, and 1306. Region 1306 is for timing delays between 0 and 60 ms, region 1304 is for delays between 60 and 120 ms, and region 1302 is for delays longer than 120 ms. The numerical ranges, such as 60 ms and 120 ms, are for illustrative purposes only. Other ranges can also be used. In one embodiment, regions 1302, 1304, and 1306 can be color-coded. For example, region 1206 can be in green to indicate "good" synchrony, region 1304 can be in yellow to indicate "OK" synchrony, and region 1302 can be in red indicating "bad" synchrony. Indicator arrow 1308 can move in real time and indicate the value of the current measured synchrony. A readout value 1310 indicates the numerical value of the timing delay.

Figure 14:
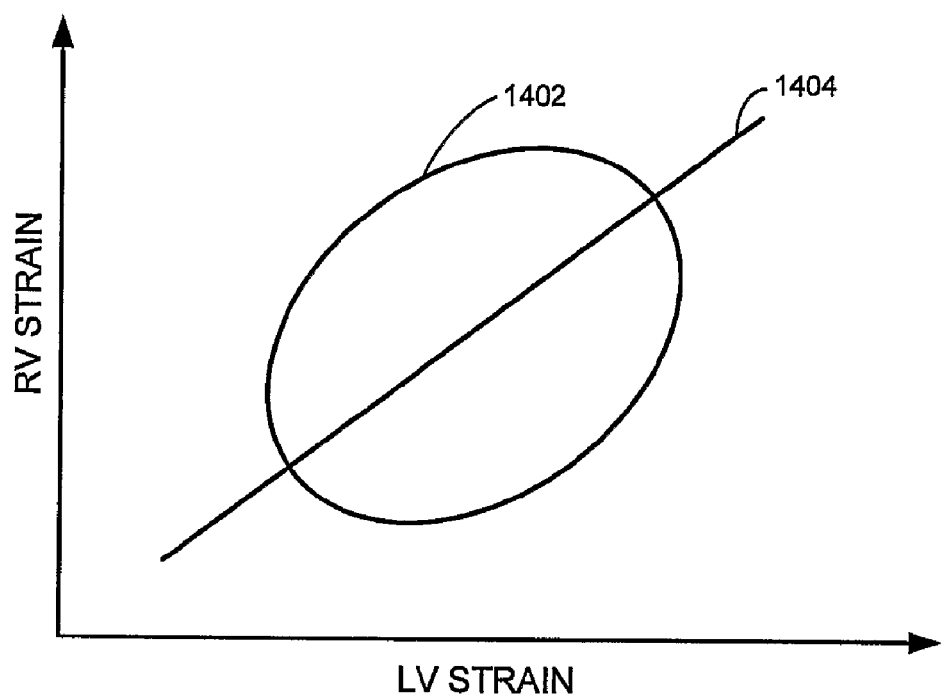
FIG. 14 is an exemplary illustration of X-Y traces of two sensor signals for purposes of displaying synchrony, in accordance with an embodiment of the present invention.
Figure 14:
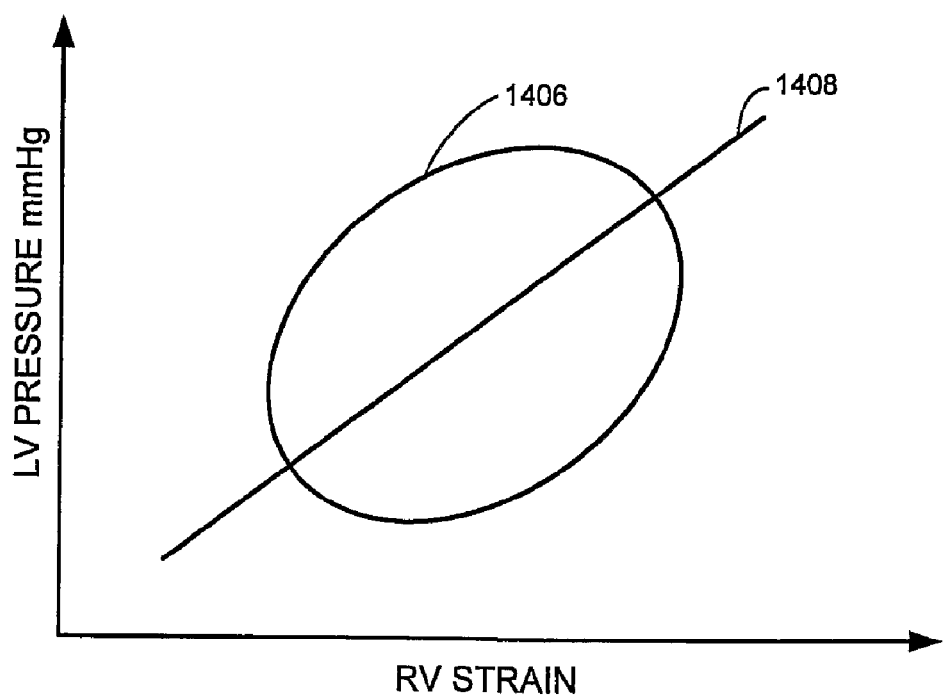

FIG. 14 is an exemplary illustration of X-Y traces of relative values of two strain sensor signals for purposes of displaying synchrony, in accordance with an embodiment of the present invention. On the upper half of FIG. 14 is a real-time X-Y plot of two sensor signals. The X-axis indicates a measured strain in the left ventricle, and the Y-axis indicates a measured strain in the right ventricle. If the contraction in the left ventricle is in complete synchrony with the contraction in the right ventricle, the resulting trace would be approximately a line 1404 angled in the upper-right direction, because the minimum and the maximum of both signals are reached at approximately the same time. If the two signals are out of synchrony to a certain degree, the resulting trace becomes more circle or oval like, such as trace 1402. If the two signals are completely out of synchrony and demonstrate a 180-degree phase difference, the resulting trace becomes approximately a line angled in the upper-left direction (not shown here).

Generally, the measured signals can include noise and distortion, and the resulting trace appears to be somewhere between a line and an oval. The more the trace resembles a line in the upper right direction, the better the synchrony. This display provides a clinician with a real-time, intuitive visual display of the synchrony without any quantitative processing. Such a qualitative presentation of synchrony does not require the use of absolute or calibrated values of sensor signals. The system uses relative and dimensionless values of two strain sensors to produce the trace. In addition, the system uses the entire signal, instead of just one point, to indicate synchrony, which helps reduce error caused by noise in the signal.

The X-Y real-time trace display can also display two calibrated signals, or a calibrated signals versus an uncalibrated signal. The lower half of FIG. 14 shows an X-Y trace of a calibrated left-ventricle pressure signal and an uncalibrated, relative right-ventricle strain signal. If the contraction in the left ventricle is in complete synchrony with the contraction in the right ventricle, the resulting trace would be approximately a line 1408 angled in the upper-right direction. If the two signals are out of synchrony, the resulting trace becomes more circle or oval like, such as trace 1406. In this example, the pressure measurement is absolute, calibrated, and dimensional (in mmHg), but the strain measurement is relative and dimensionless.

Figure 15:
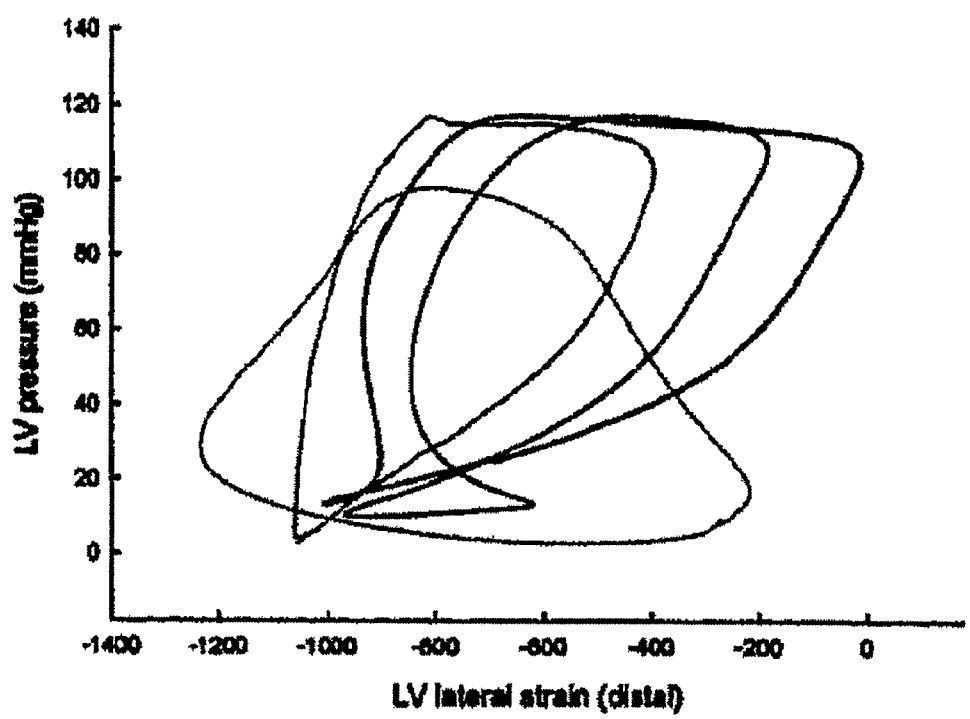
FIG. 15 illustrates an X-Y trace of left-ventricle pressure versus left-ventricle lateral strain based on actual data collected by uncalibrated sensors placed in a pig's heart, in accordance with an embodiment of the present invention.
Figure 16:
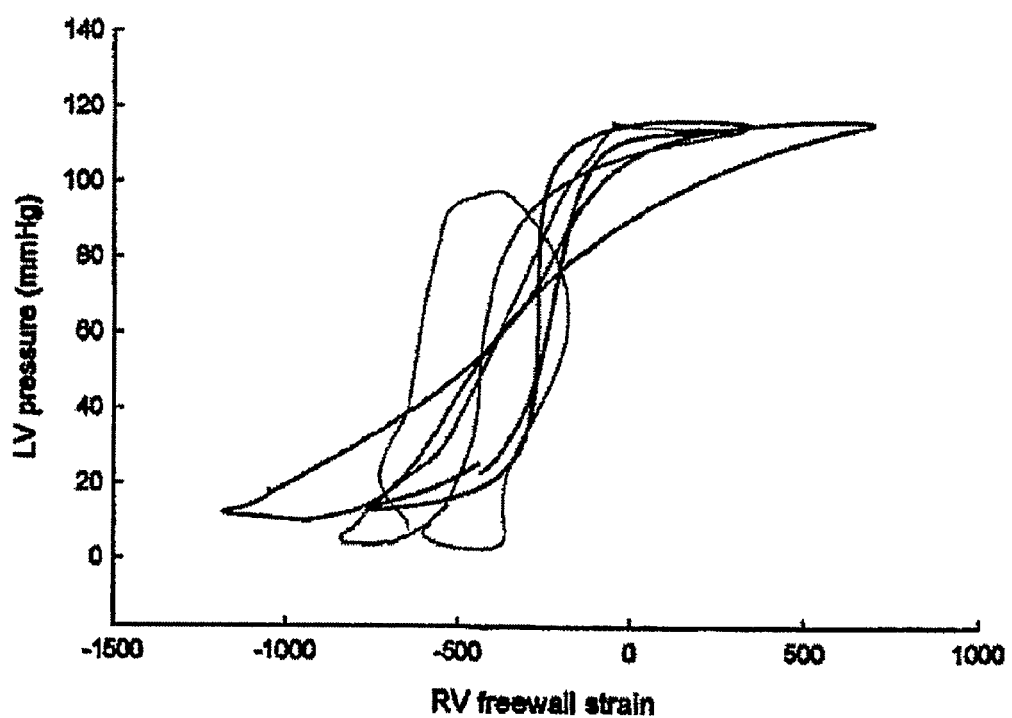
FIG. 16 illustrates an X-Y trace of left-ventricle pressure versus right-ventricle freewall strain based on actual data collected by uncalibrated sensors placed in a pig's heart, in accordance with an embodiment of the present invention.
Figure 17:
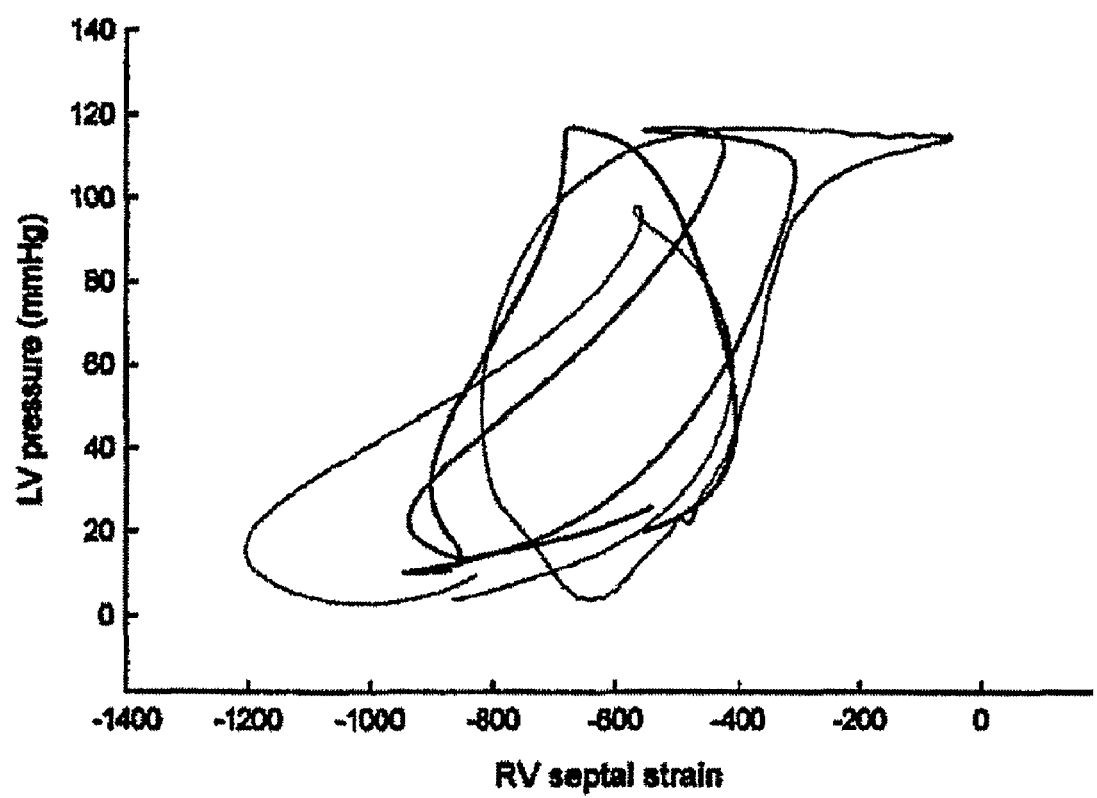
FIG. 17 illustrates an X-Y trace of left-ventricle pressure versus right-ventricle septal strain based on actual data collected by uncalibrated sensors placed in a pig's heart, in accordance with an embodiment of the present invention.

FIG. 15-17 illustrate actual real-time X-Y traces with various sensor signals measured in a pig's heart. FIG. 15 is a trace of the left-ventricle pressure versus left-ventricle lateral strain, FIG. 16 is a trace of the left-ventricle pressure versus right-ventricle freewall strain, and FIG. 17 is a trace of the left-ventricle pressure versus the right-ventricle septal strain.

Figure 18:
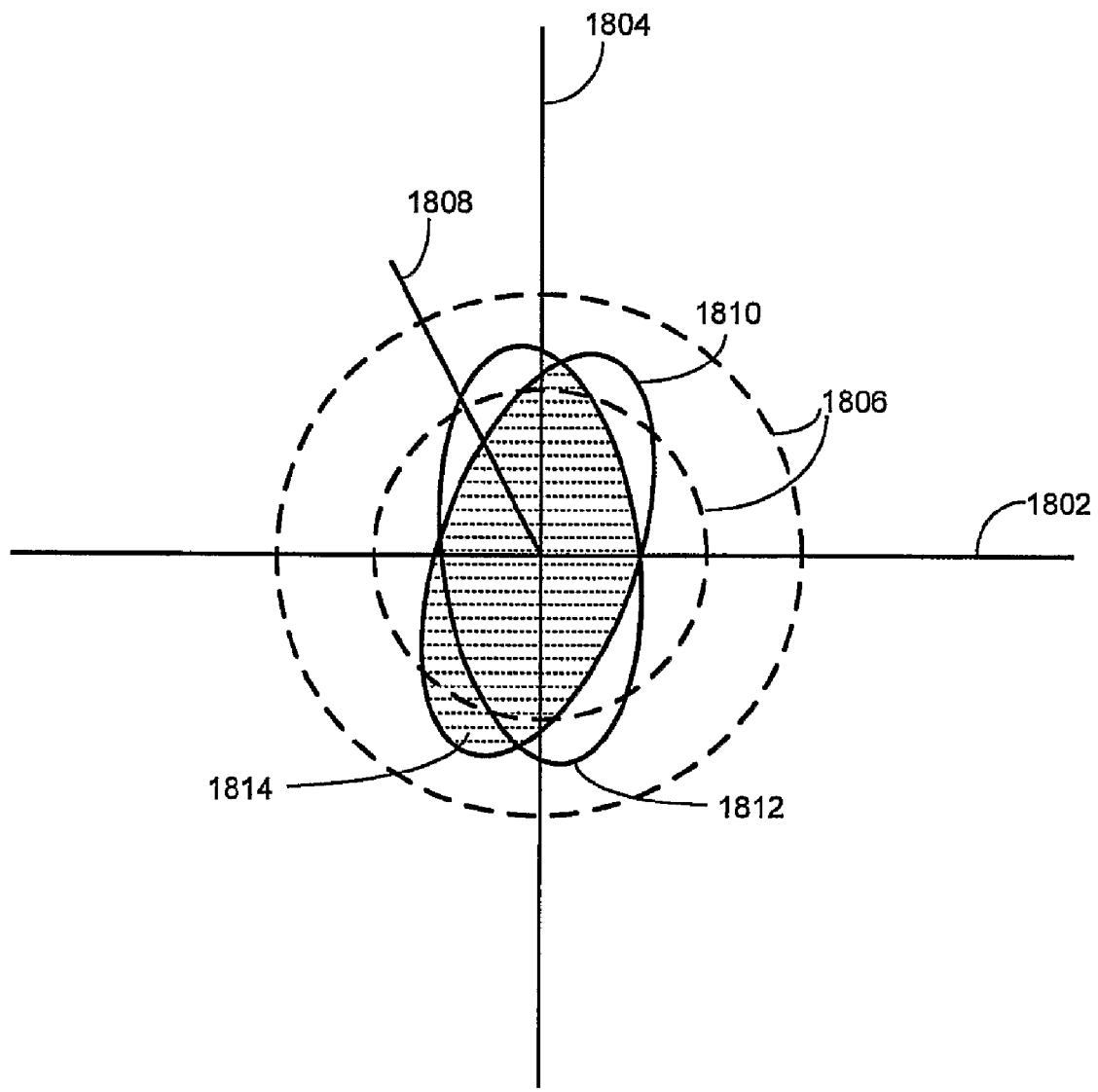
FIG. 18 is an exemplary illustration of a radar-scan-like display of two sensor signals for indicating synchrony, in accordance with an embodiment of the present invention.

FIG. 18 is an exemplary illustration of a radar-scan-like display of two sensor signals for indicating synchrony, in accordance with an embodiment of the present invention. This display provides a sweeping arm 1808 that rotates one revolution for each heartbeat cycle. The display includes an origin, which is the intersection of two orthogonal axes, 1802 and 1804. Sweeping arm 1808 rotates around the origin. As sweeping arm 1808 sweeps in real time, signal amplitude is indicated by a radial distance from the origin. The instant signal amplitude is traced along sweeping arm 1808 with a corresponding radial distance. Magnitude guides 1806 are provided to allow a user to more easily comprehend the magnitude of the signals.

Sweeping arm 1808 can trace multiple signals simultaneously. The exemplary display in FIG. 18 shows a first trace pattern 1810 from a first signal and a second trace pattern 1812 from a second signal. Pattern 1810 and pattern 1812 overlap, forming an overlapping region 1814 which is shaded. The area of region 1814 indicates the degree to which the two signals move in synchrony. In one embodiment, trace patterns 1810 and 1812 are each color coded, and overlapping region 1814 is highlighted to facilitate easy observation. In a further embodiment, the signals being traced are first normalized for accurate comparison. Normalization, however, can be optional so that less processing is required.

Figure 19:
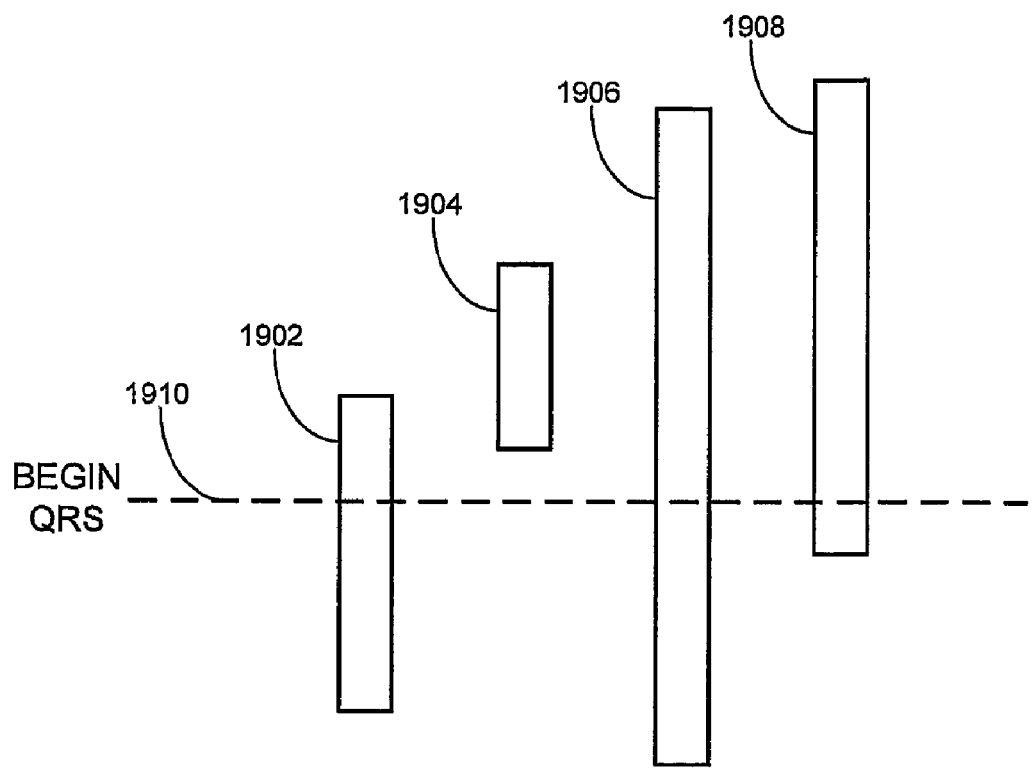
FIG. 19 is an exemplary illustration of a graphic-equalizer-like display of multiple sensor signals for indicating synchrony, in accordance with an embodiment of the present invention.

FIG. 19 is an exemplary illustration of a graphic-equalizer-like display of multiple sensor signals for indicating synchrony, in accordance with an embodiment of the present invention. A horizontal axis 1910 represents a reference time, which in one embodiment can be the beginning time of the QRS complex. QRS complex refers to the principal deflection in the ECG, representing ventricular depolarization. This equalizer-like display includes four channel indicators, 1902, 1904, 1906, and 1908. Each channel represents a sensor signal. For example, each channel can represent a signal from one of four strain sensors. Further, one channel can represent a strain sensor signal, a second channel can represent a pressure sensor signal, a third channel can represent a volume flow meter signal, and a fourth channel can represent an accelerometer signal. These channel indicators resemble a graphic equalizer indicator, which is commonly present on consumer audio equipment, making the display intuitive to an observer.

Figure 20:
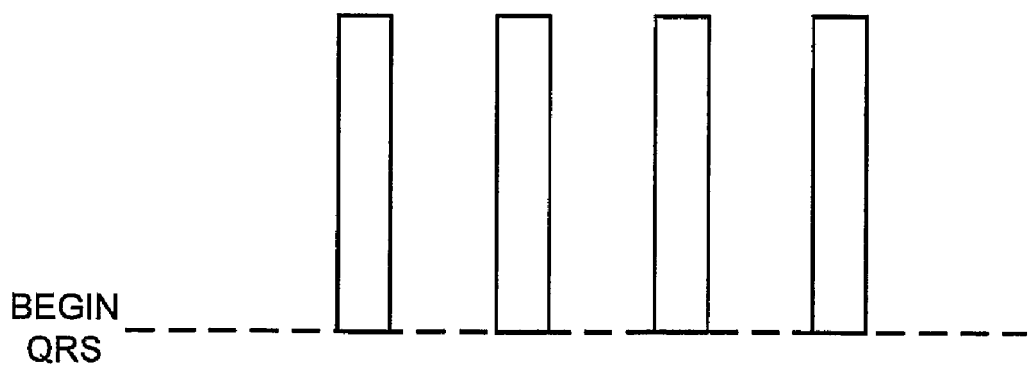
FIG. 20 is an exemplary illustration of a graphic-equalizer-like display of multiple sensor signals indicating substantial synchrony, in accordance with an embodiment of the present invention.

The bottom of a channel indicator corresponds to a first characteristic event in the signal represented by the channel indicator. An example of such first characteristic event is the signal maximum. In one embodiment, the first characteristic event occurs at approximately the same time as the beginning of the QRS complex. The top of each channel indicator represents a second characteristic event in the signal. An example of such second characteristic event is the signal minimum. When the heart is in good synchrony, different channel indicators, which represent different sensor signals, are substantially even with each other. The four signals represented in FIG. 19 are not in good synchrony, because the bottom of these indicators are not close to the beginning of the QRS complex, and their top are not even with each other. In contrast, the four signals shown in FIG. 20 demonstrate good synchrony, because the four channel indicators are substantially even with each other.

The graphic-equalizer-like display can also operate in conjunction with an audio device. The audio device uses a tone to indicate the degree of synchrony, wherein a higher frequency of the tone indicates better synchrony. In a further embodiment, the audio device can create a beating sound for each channel to indicate the degree synchrony.

Measuring Electromechanical Delay (EMD)

Embodiments of the present invention measure the electromechanical delay (EMD) between an ECG signal and a sensor signal to evaluate the cardiac synchrony. In general, a finite period exists between the start of an electrical activity and the start of a mechanical event in response. This period is referred to as EMD. EMD can be used to indicate the degree of synchrony in a heart.

Figure 21:
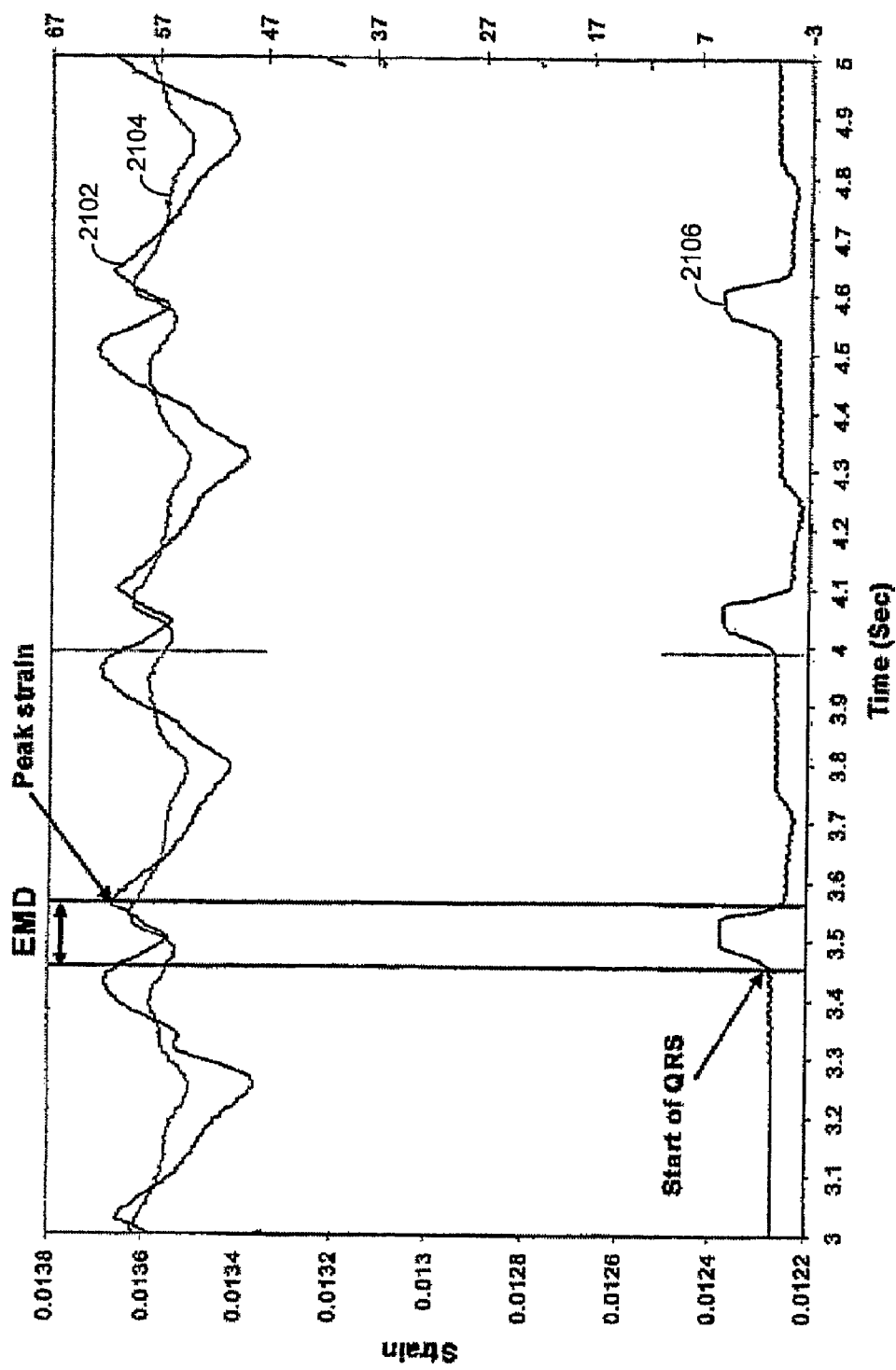
FIG. 21 illustrates a measurement of electromechanical delay (EMD) for measuring synchrony, in accordance with an embodiment of the present invention.

FIG. 21 illustrates a measurement of EMD for measuring synchrony, in accordance with an embodiment of the present invention. In this example, a left-ventricle distal strain sensor, such as sensor 107 as is shown in FIG. 1, generates a signal 2102. A second more proximal strain sensor in the left ventricle, such as the third strain sensor 106 as is shown in FIG. 1, generates a second signal 2104. Both signals 2102 and 2104 are uncalibrated. The EMD is defined as a time delay between a characteristic point of an ECG signal 2106 and a characteristic point on one of the sensor signals. In this case, the characteristic point of ECG signal 2106 is the start of the QRS complex. The characteristic point of a signal is the periodical signal peak. The time difference between the two characteristic points, $\Delta t$, is the EMD for the signal.

The system can measure EMD by subtracting the starting time of the QRS complex from the peak time of a sensor signal. The system can further apply thresholds to determine quality of the synchrony. For example, the system may use a set of thresholds x and y. For $\Delta t < x$, the synchrony is designated as "good;" for $x < \Delta t < y$, the synchrony is designated as "OK;" and for $y < \Delta t$, the synchrony is designated as "bad."

Figure 22:
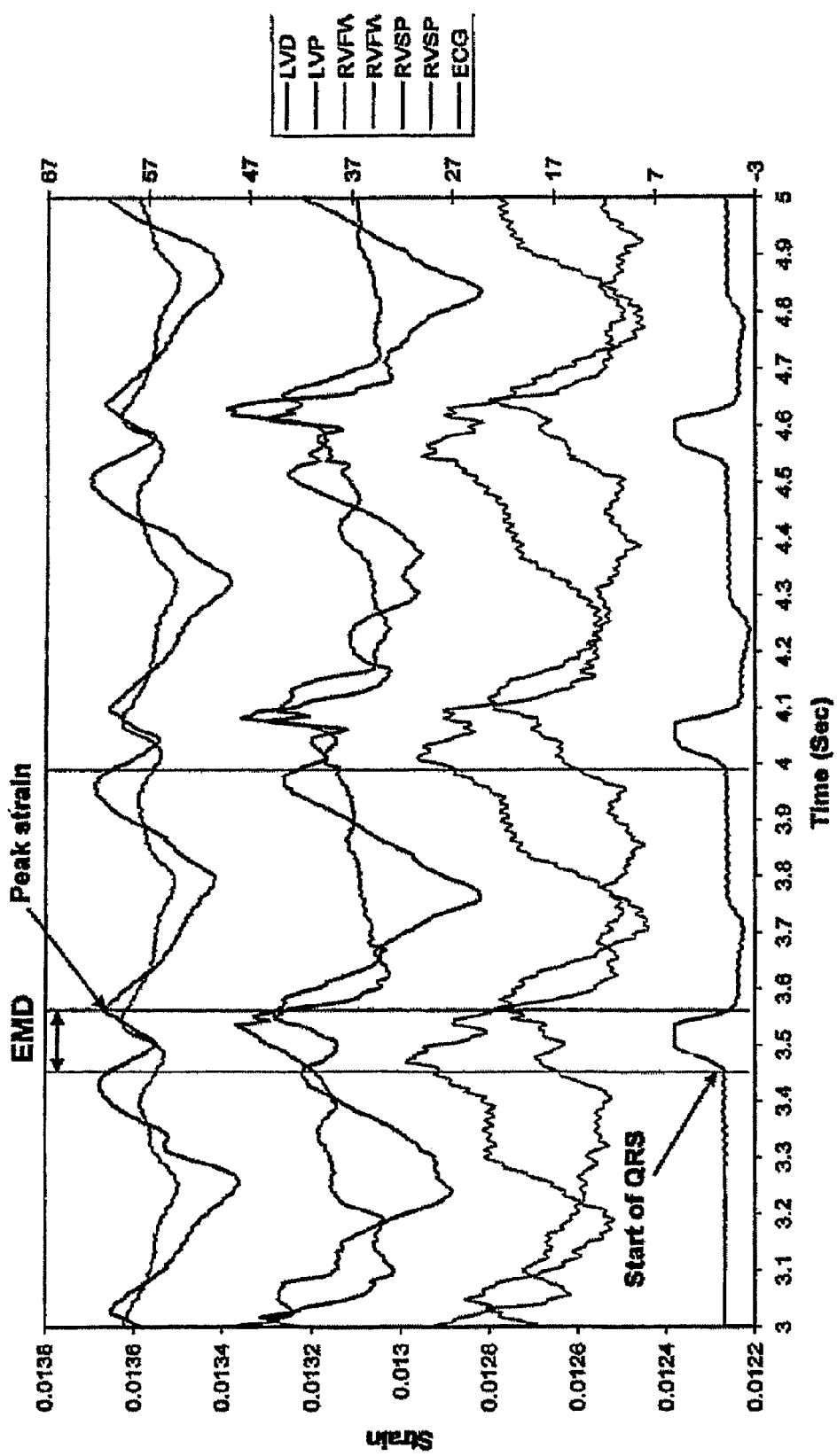
FIG. 22 illustrates a measurement of EMD based on one of multiple strain gauge signals for measuring synchrony, in accordance with an embodiment of the present invention.

FIG. 22 illustrates a measurement of EMD based on an uncalibrated strain gauge signal from a pig's heart, in accordance with an embodiment of the present invention.

Graphic User Interface

Figure 23:
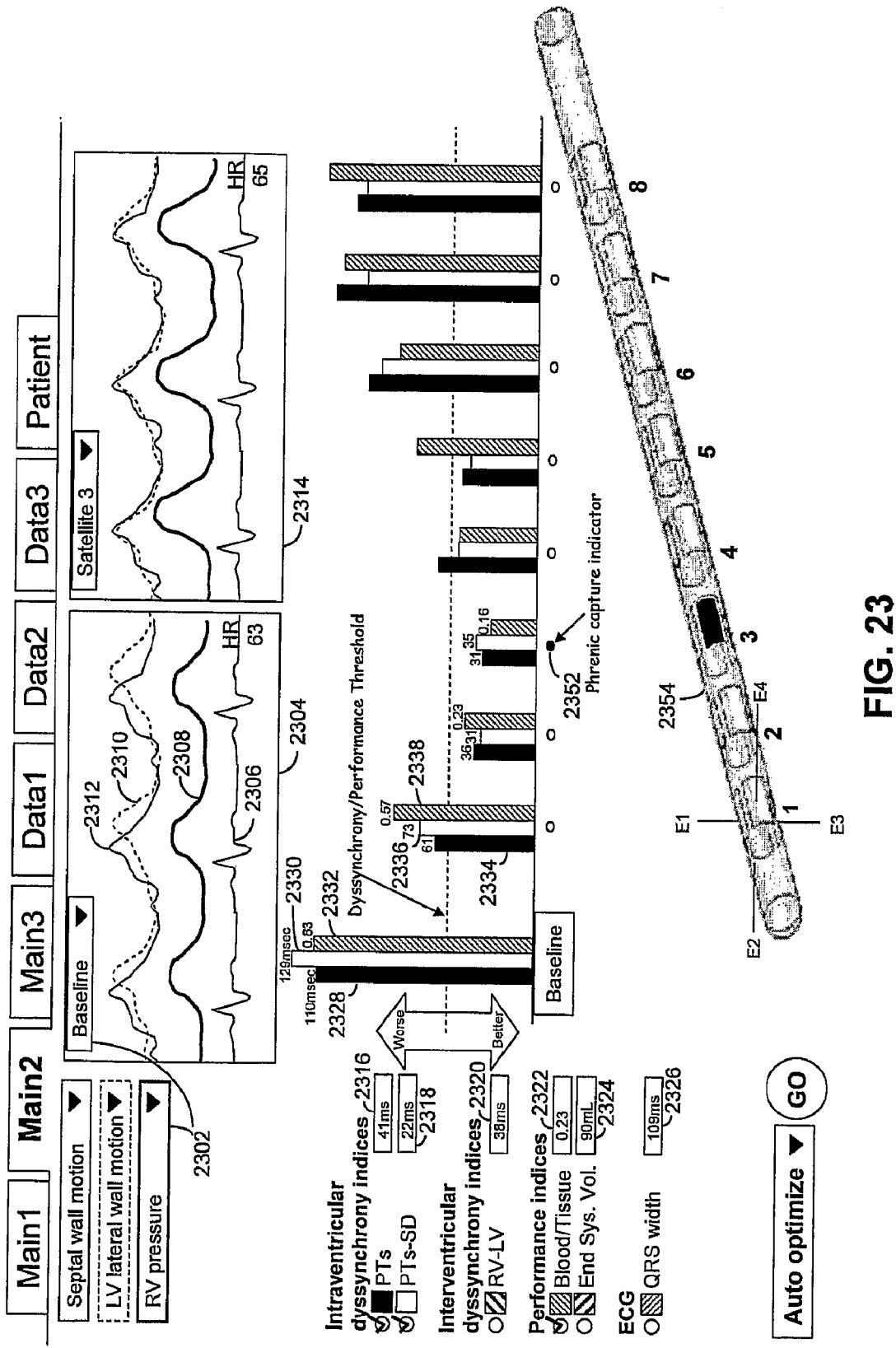
FIG. 23 illustrates an exemplary graphic user interface (GUI) for configuring a multi-electrode pacing lead and for displaying measured signals, in accordance with an embodiment of the present invention.

FIG. 23 illustrates an exemplary graphic user interface (GUI) for configuring a multi-electrode pacing lead and for displaying measured signals, in accordance with an embodiment of the present invention. This GUI can be used for configuring electrodes and timing pace signals transmitted over a multiple electrode lead 2354. A user can interact with a pacing control system through this GUI using a keyboard, mouse, or touch screen. This GUI also allows the user to select and observe different dyssynchrony and performance indices to be optimized.

The dyssynchrony indices can include intraventricular and interventricular dyssynchrony indices. The intraventricular dyssynchrony indices can further include a Proteus Time to Systolic Contraction (PTs) index, which is the time interval between onset of QRS complex of an ECG signal and onset of systolic initiation. Typically, a low PTs value indicates good synchrony. A numeric display 2328, which shows an exemplary value of 43 ms, is provided for this time interval. The intraventricular dyssynchrony indices can indicate the time of contraction of the left ventricle relative to the septum, which can be measured by using leads 105 and 102 as is shown in FIG. 1. The system can use various sensors, including strain gauges, to obtain this measurement.

A second intraventricular dyssynchrony index is the Proteus Time to Systolic contraction Standard (PTs-SD). After measuring the PTs indices of a number of locations, the system can compute the standard deviation of these measurement as an index for dyssynchrony. Low PTs-SD values indicate good synchrony. The GUI also provides a numeric display 2318 which shows the numeric value of this index.

The GUI further provides an interventricular dyssynchrony index, which presents the timing delay between a global indicator for the right ventricle and a global indicator for the left ventricle (RV-LV). The GUI provides a numeric display 2320 to show the numeric value thereof. A global indicator can be the signal from a pressure sensor or other types of sensors.

The GUI also provides performance indices. The first performance index is the blood tissue ratio. To measure the blood tissue ratio, the system can provide two electric fields, one at a low frequency and the other at a high frequency. Because blood and tissue have different impedance depending on the frequency of the electric field, the system can determine the relative amount of blood and tissue between two points. When the heart contracts, blood is ejected, the amount of blood decreases, and the tissue thickens. Consequently, the blood to tissue ratio decreases. The GUI provides a numeric display 2322 to show the numeric value of the blood to tissue ratio.

A second performance index is the end systolic volume. In one embodiment, the system uses electrodes to both generate and detect electric fields to measure approximate systolic volume in real time. A numeric display 2324 provides the numeric value of the systolic volume.

The GUI also provides an ECG index. A numeric display 2326 shows the numeric value of the QRS width.

In the illustrated example, for all the indices shown on the GUI, the lower the index value the better the performance of the heart. Therefore, the goal is to minimize these indices.

The GUI provides a three-dimensional illustration of a multi-electrode lead 2354. In this example, lead 2354 includes eight satellites, and each satellite includes four electrodes, such as E1, E2, E3, and E4 on the first satellite. Other numbers of satellites and electrodes are also possible. The GUI further provides an automatic optimization button 2327, labeled "GO." When GO button 1748 is selected, the system paces through each satellite with all four electrodes. Pulses transmitted through each satellite provide sufficiently high voltage for cardiac pacing.

The GUI uses a bar graph to display the selected dyssynchrony and performance indices for a baseline measurement (without pacing) and for when each satellite is pulsed. In one embodiment, the bar graphs are aligned with their corresponding satellites. In the left-most bar graph, which display baseline measurements, a first bar 2328 indicates the PTs value, a second bar 2330 indicates the PTs-SD value, and a third bar 2332 indicates the blood tissue ratio. Similarly, in a second graph for measuring indices when a pacing signal is applied to satellite 1, a first bar 2334 indicates the PTs value, a second bar 2336 indicates the PTs-SD value, and a third bar 2338 indicates a blood tissue ratio. Bar graphs are generated for all eight satellites. In this example, satellite 3 exhibits the lowest selected indices, which indicates the least dyssynchrony and therefore is the optimal pacing location.

A physician may notice the presence of phrenic capture during the pacing of satellite 3. In such a case, the physician may select a phrenic capture indicator 2352. In response, the system cycles through all the electrodes or combination of electrodes on satellite 3 to find an electrode or a combination of electrodes that does not cause phrenic nerve capture while still pacing the heart. For example, the four electrodes on satellite 3 are able to provide at least eight combinations that define eight circumferential directions for pacing. These eight electrode combinations may be individual electrodes paired with adjacent electrodes, which can be used to obtain a field in the direction between the electrode pair.

The GUI also provides displays for various selected signals. For example, a first graph 2304 is provided for baseline measurements and a second graph 2314 is provided for measurements corresponding to satellite 3. In graph 2304, a first plot 2312 indicates the septal wall motion, a second plot 2312 indicates the left-ventricle wall motion, a third plot 2308 indicates the right-ventricle pressure, and a fourth plot 2306 indicates the ECG. Pull-down menus 2302 are provided to change the graphs to display dyssynchrony from other satellites and to allow display of other indices.

Figure 24:
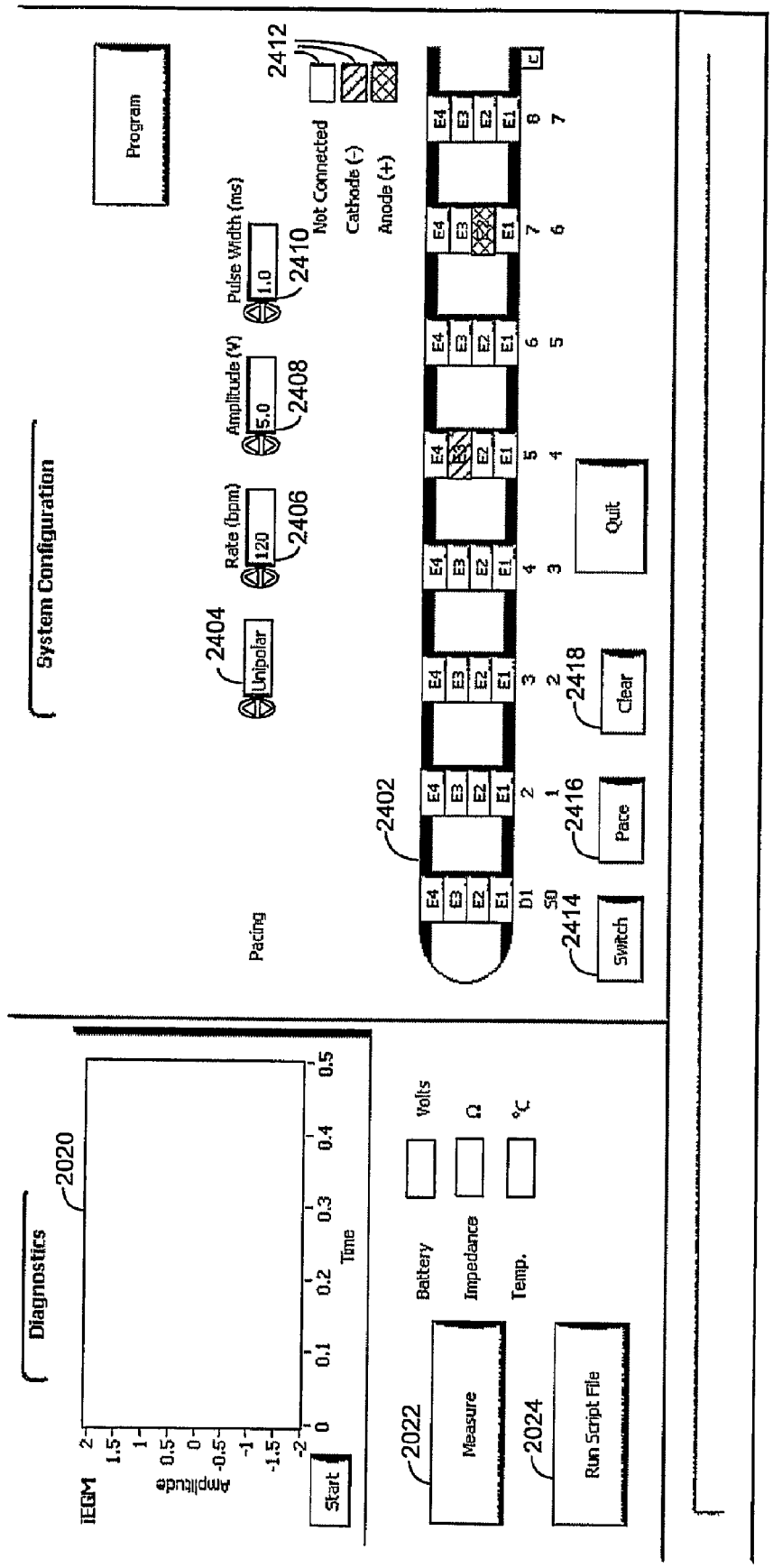
FIG. 24 illustrates another exemplary GUI for configuring a multi-electrode pacing lead, in accordance with an embodiment of the present invention.

FIG. 24 illustrates another exemplary GUI for configuring a multi-electrode pacing lead, in accordance with an embodiment of the present invention. This GUI provides a two-dimensional illustration of a multi-electrode pacing lead 2402. Also illustrated on lead 2402 are the satellites and the four electrode, denoted as E1-E4, on each satellite.

A user can select a particular electrode by clicking on that electrode. In one embodiment, the state of the electrode changes with each click. For example, with one click, the electrode is to be coupled to a cathode; with two clicks, the electrode is to be coupled to the anode; and with three clicks, the electrode is to be unconnected. The state of the electrode can be indicated by its color, and a color legend 2412 indicates the correlation between a color and a connection state.

The GUI also provides four selection fields for configuring pacing parameters. A first selection field 2404 allows the user to specify polarity of the pacing signal. A second selection field 2406 allows the user to specify the pacing rate (bpm). A third selection field 2408 allows the user to specify the amplitude of the pacing signal. A fourth selection field 2410 allows the user to specify the pulse width of the pacing signal.

A switch button 2414, when clicked, changes the connection state of the pacing lead based on the electrode selections made by the user. A pace button 2416, when clicked, commences the pacing based on the parameters provided by the user. A clear button 2418, when clicked, stops the pacing and resets the connection state.

The GUI also provides a region 2020 for displaying intracardiac electrogram (iEGM). In addition, the GUI provides a measure button 2022, which, when clicked, measures certain parameters of the pacing system, such as the battery voltage, the lead impedance, and the lead temperature. Also provided with the GUI is a "Run Script File" button 2024. When this button is clicked, the system allows the user to specify a script file, based on which the system automatically executes a series of pacing and testing with parameters given in the script file.

Embodiments of the present invention also provide a GUI for displaying electric signals detected through different electrodes in an electric tomography application. In an electric tomography application, an electric field is applied to the heart. This field can be provided by, for example, two electrodes on a lead or by an external source. Other electrodes on the lead can then pick up a signal induced by the field, wherein the amplitude of the signal depends on the location of the detecting electrode. Therefore, the induced signal on an electrode indicates the location and movement of the electrode.

Figure 25:
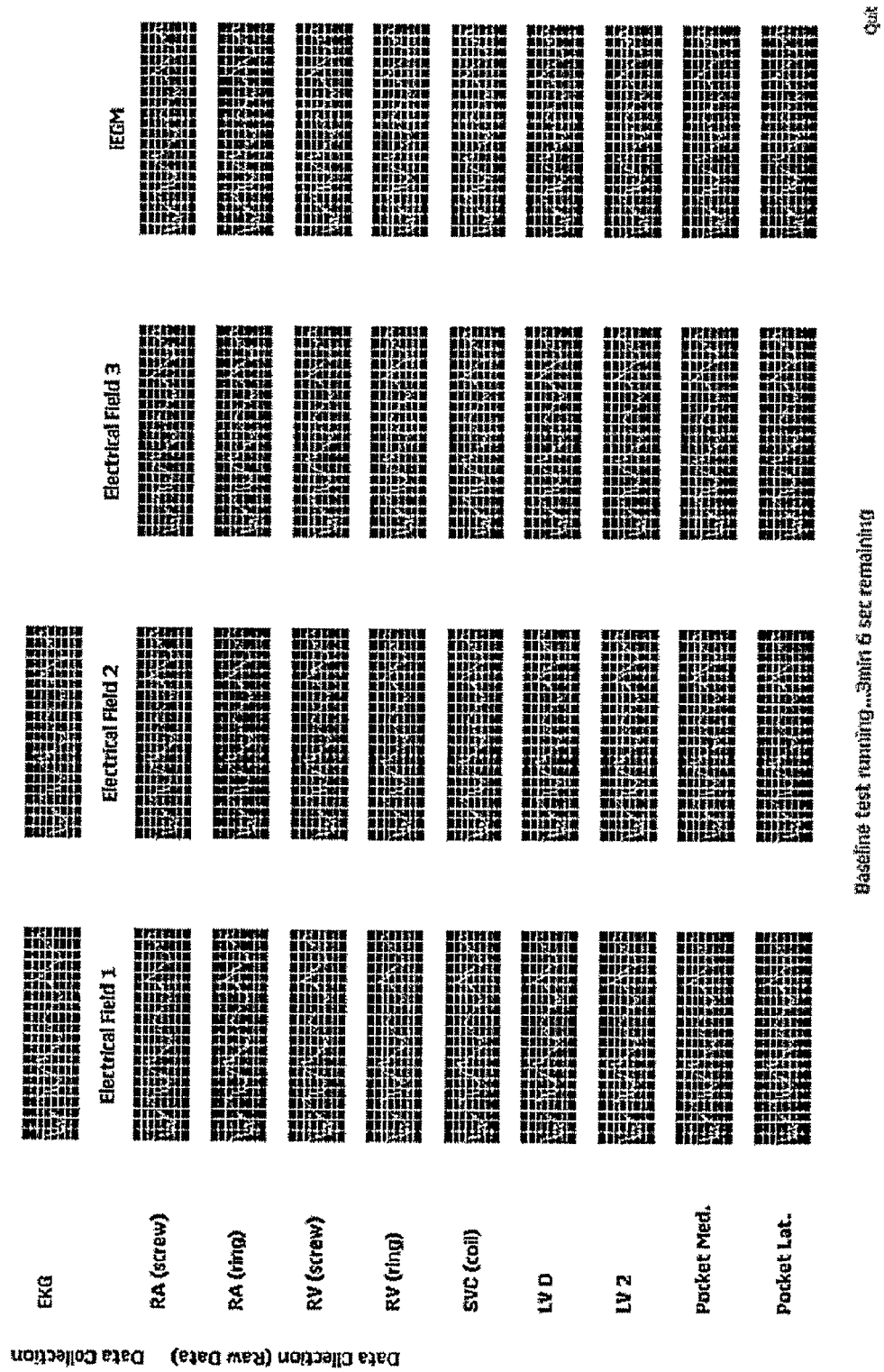
FIG. 25 is an exemplary illustration of a display showing raw data collected from different electrodes in response to different electric fields in an electric tomography measurement, in accordance with an embodiment of the present invention.

FIG. 25 is an exemplary illustration of a display showing raw data collected from different electrodes in response to different electric fields in an electric tomography measurement, in accordance with an embodiment of the present invention. The GUI as illustrated in FIG. 25 displays raw data of field-induced signals detected by electrodes placed at various locations. The display also includes different signals induced by different fields.

Figure 26:
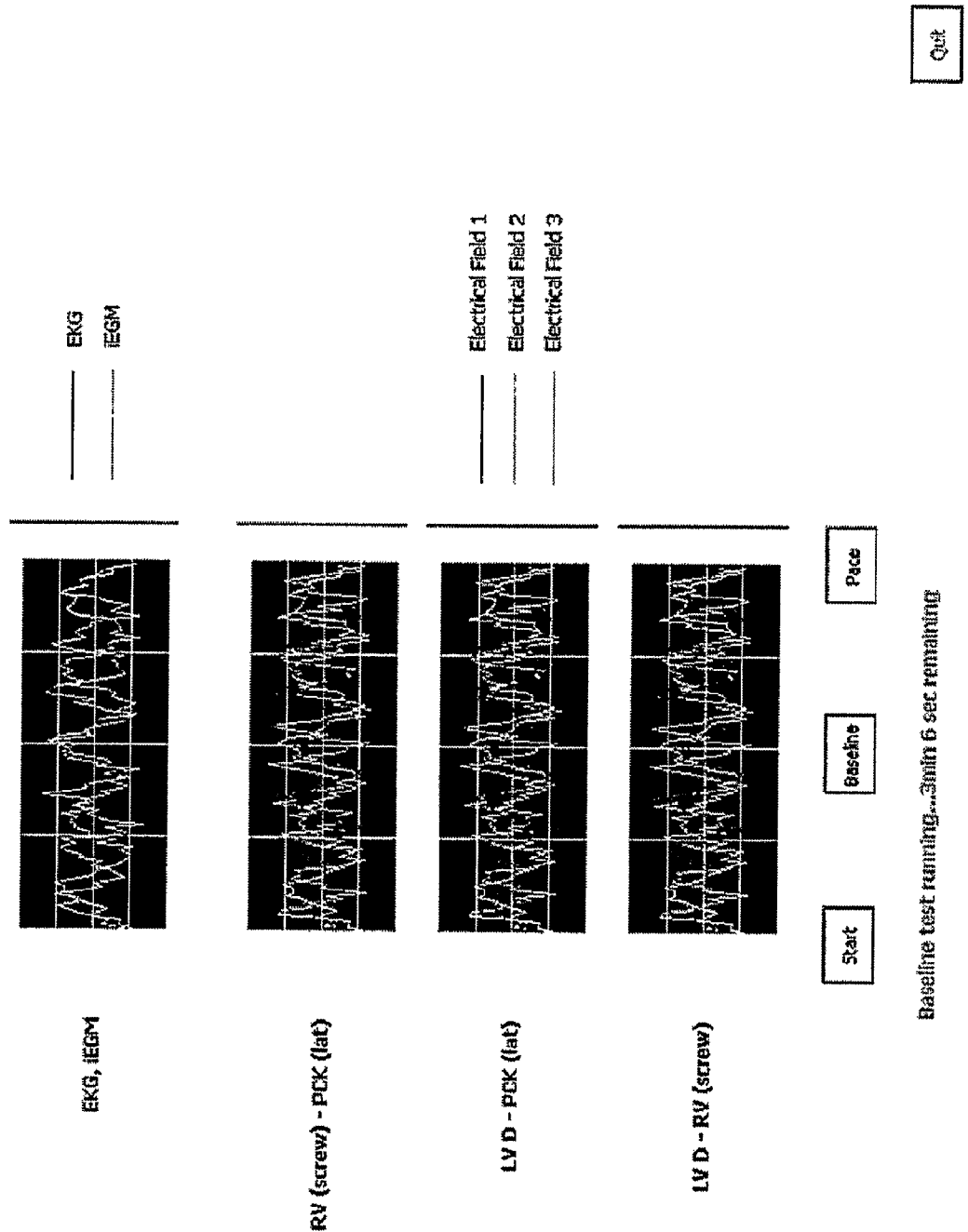
FIG. 26 is an exemplary illustration of a display showing comparison of data collected from different electrodes in response to different electric fields in an electric tomography measurement, in accordance with an embodiment of the present invention.

FIG. 26 is an exemplary illustration of a display showing comparison of data collected from different electrodes in response to different electric fields in an electric tomography measurement, in accordance with an embodiment of the present invention. The display also allows the user to select different signals, such as the EKG and iEGM, to be displayed simultaneously for comparison.

Figure 27:
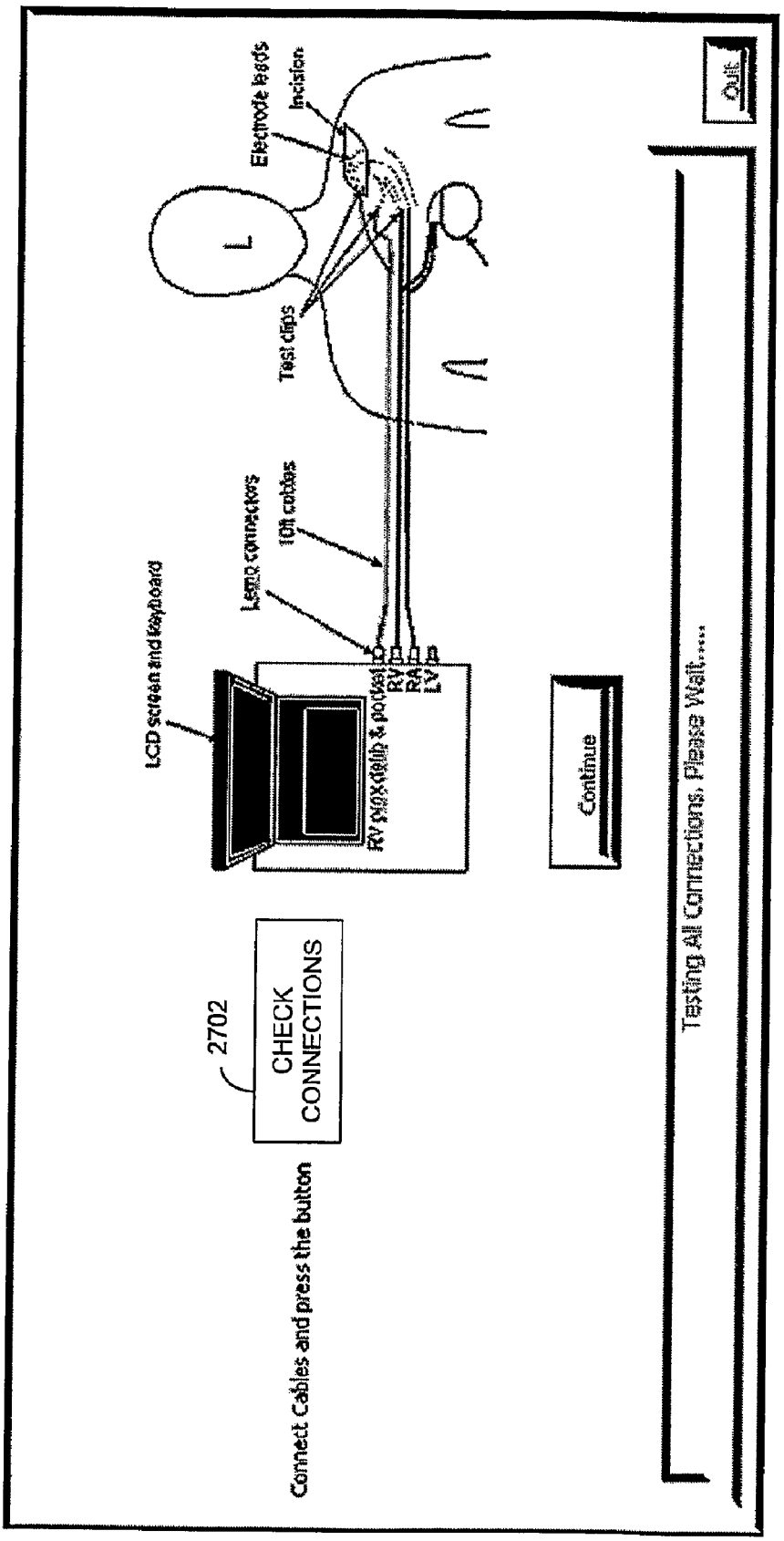
FIG. 27 illustrates an exemplary GUI for confirming connectivity between the pacing system, the pacing leads, and the pacing electrodes, in accordance with an embodiment of the present invention.

FIG. 27 illustrates an exemplary GUI for confirming connectivity between the pacing system, the pacing leads, and the pacing electrodes, in accordance with an embodiment of the present invention. The GUI provides an illustration of the wires or cables coupling the pacing leads to the pacing-control system, which, in this example, is an external computer. The GUI also provides a "check connection" button 2702, which, when clicked, issues a command to check the illustrated connectivity. If a connection appears to have failed, the GUI can issue a warning. In one embodiment, this warning is represented by a change of color of the failed wire or cable.

Figure 28:
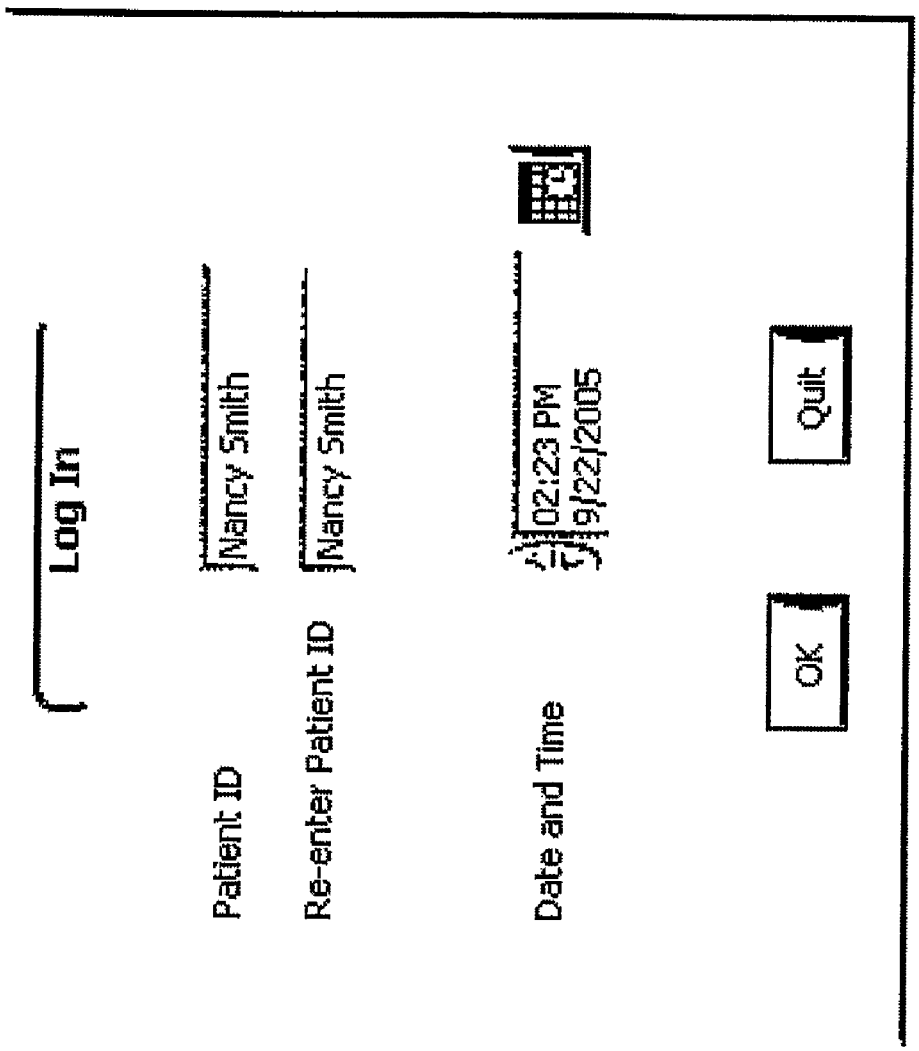
FIG. 28 illustrates an exemplary GUI for logging in and loading saved cardiac pacing and measurement data of a patient, in accordance with an embodiment of the present invention.
Figure 29:
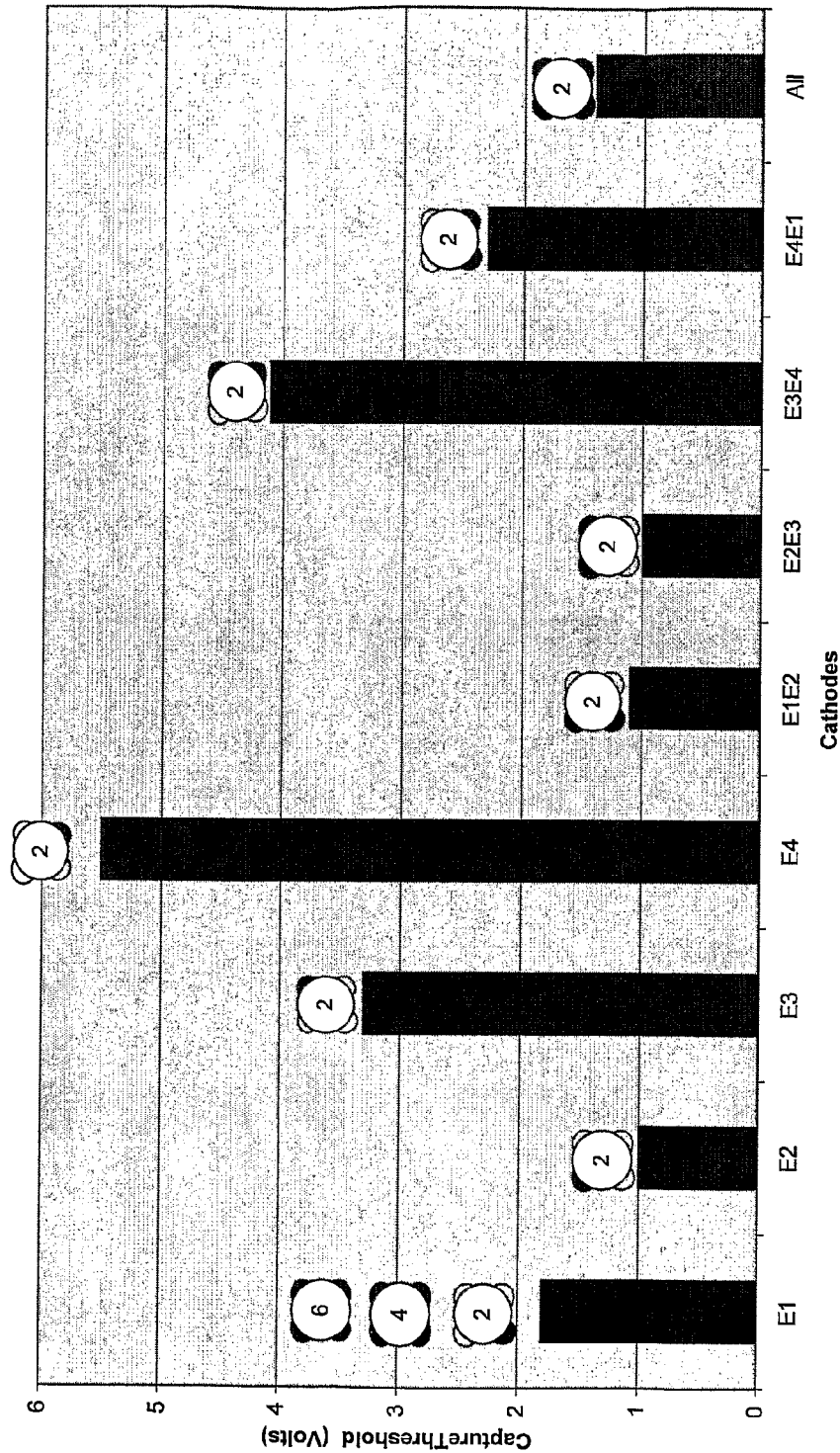
FIG. 29 is a Pacing Capture Chart which illustrates an exemplary GUI where, Green dots mean Anode, Red dots mean Cathode, and the number in the middle of the circle is the satellite number.
Figure 26:
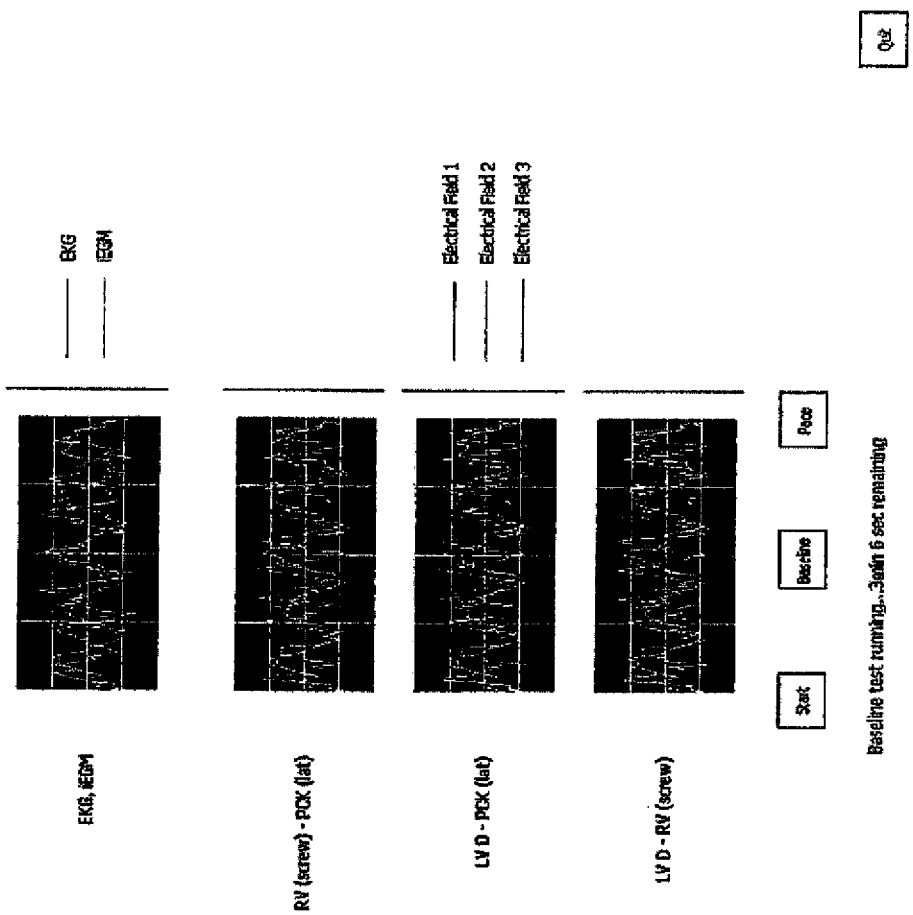

FIG. 28 illustrates an exemplary GUI for logging in and loading saved cardiac pacing and measurement data of a patient, in accordance with an embodiment of the present invention. A physician can specify a patient's identifier, as well as the time and date when the data was stored. In a further embodiment, the log-in GUI can also provide a password field for increased security.

Embodiments of the present invention can be used in various systems. Such systems may include various types of sensors. Such sensors and systems have been described in various applications by some of the present inventors. These applications also describe multiplexing systems previously developed by some of the present inventors with which the present invention can be employed. These applications include: U.S. patent application Ser. No. 10/734,490 published as 20040193021 titled: "Method And System For Monitoring And Treating Hemodynamic Parameters"; U.S. patent application Ser. No. 11/219,305 published as 20060058588 titled: "Methods And Apparatus For Tissue Activation And Monitoring"; International Application No. PCT/US2005/046815 titled: "Implantable Addressable Segmented Electrodes"; U.S. patent application Ser. No. 11/324, 196 titled "Implantable Accelerometer-Based Cardiac Wall Position Detector"; U.S. patent application Ser. No. 10/764, 429, entitled "Method and Apparatus for Enhancing Cardiac Pacing," U.S. patent application Ser. No. 10/764,127, entitled "Methods and Systems for Measuring Cardiac Parameters," U.S. patent application Ser. No. 10/764,125, entitled "Method and System for Remote Hemodynamic Monitoring"; International Application No. PCT/US2005/046815 titled: "Implantable Hermetically Sealed Structures"; U.S. application Ser. No. 11/368,259 titled: "Fiberoptic Tissue Motion Sensor"; International Application No. PCT/US2004/041430 titled: "Implantable Pressure Sensors,"; U.S. patent application Ser. No. 11/249,152 entitled "Implantable Doppler Tomography System," and claiming priority to: U.S. Provisional Patent Application No. 60/617, 618; International Application Serial No. PCT/USUS05/39535 titled "Cardiac Motion Characterization by Strain Gauge". These applications are incorporated in their entirety by reference herein.

The foregoing descriptions of embodiments of the present invention have been presented for purposes of illustration and description only. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

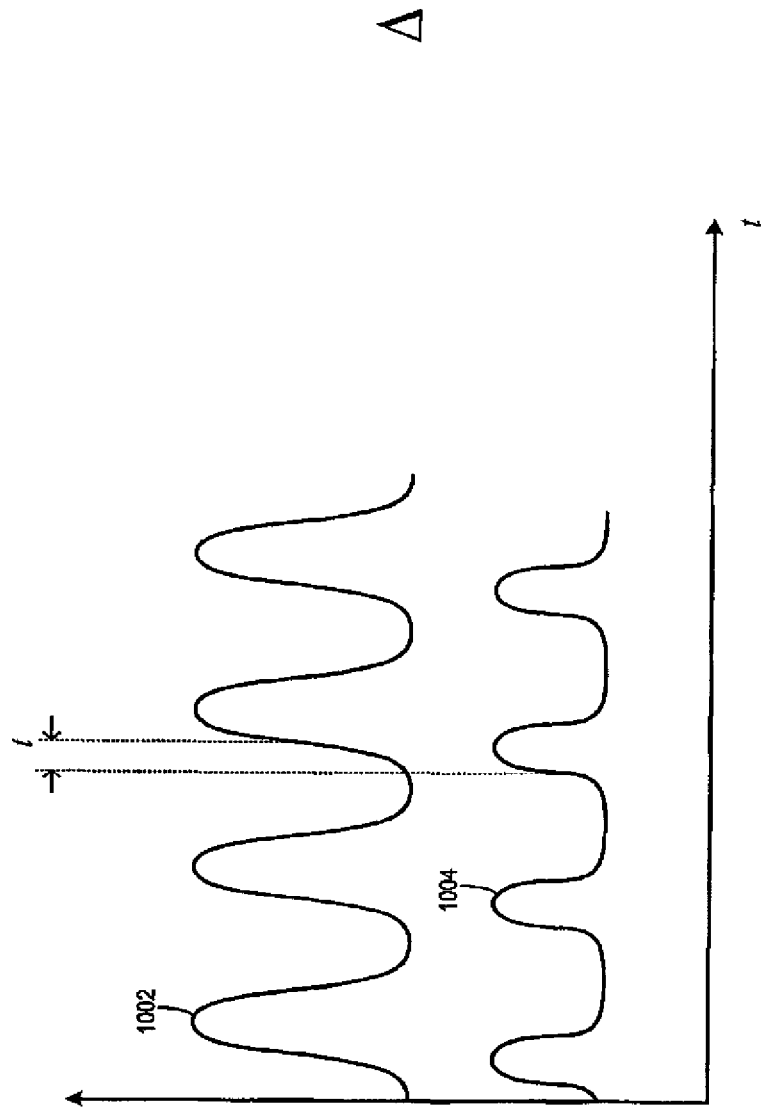

What is claimed is:

1. A method to perform automatic optimization of cardiac resynchronization therapy (CRT), the method comprising:
    performing a first set of iterations to select at least one satellite from a plurality of satellites formed on at least one pacing lead inserted in a patient, wherein each satellite of the plurality of pacing satellites comprises:
    a plurality of electrodes; and
    a control chip communicatively coupled to each electrode of the plurality of electrodes;
    performing a second set of iterations to select at least one electrode from each one of the at least one satellite selected from the plurality of satellites when the at least one electrode in the each one of the at least one satellite is addressed and controlled through a respective control chip of the each one of the at least one satellite upon a receipt of configuration signals configured to select the at least one electrode; and
    performing a third set of iterations to select at least one timing configuration for pacing signals transmitted through the at least one electrode on the each one of the at least one satellite.

2. The method of claim 1, wherein the plurality of electrodes comprise at least one sensor.

3. The method of claim 2, wherein the at least one sensor is an accelerometer, a strain gauge, an angle gauge, a pressure sensor, or a temperature sensor.

4. The method of claim 1, wherein the performing the first set of iterations comprises:
    iteratively transmitting a pacing signal through the plurality of satellites, wherein each iteration of the transmitting the pacing signal is performed on a different satellite in the plurality of satellites; and
    selecting the at least one satellite based on a cardiac response resulting from the pacing signal through the plurality of satellites.

5. The method of claim 4, wherein the configuration signals are forwarded from a pacing can communicatively coupled to the each electrode of the plurality of electrodes in the each satellite, and wherein the iteratively transmitting the pacing signal through the plurality of satellites comprises iteratively transmitting the pacing signal from the pacing can as a signal source and the plurality of satellites as a signal sink.

6. The method of claim 5, wherein the pacing can and the plurality of satellites are electrically coupled via a two-wire conductor formed along the at least one pacing lead.

7. The method of claim 4, wherein the iteratively transmitting the pacing signal through the plurality of satellites is performed using a first set of the plurality of satellites as a signal source and a second set of the plurality of satellites as a signal sink.

8. The method of claim 4, wherein the selecting the at least one satellite based on the cardiac response comprises determining an occurrence of a cardiac contraction in response to the pacing signal.

9. The method of claim 1, wherein the performing the second set of iterations comprises:
    iteratively transmitting a pacing signal through the plurality of electrodes on the each one of the at least one satellite, wherein each iteration of the transmitting the pacing signal is performed on a different electrode in the plurality of electrodes; and
    selecting the at least one electrode based on a cardiac response resulting from the pacing signal through the plurality of electrodes.

10. The method of claim 9, wherein the configuration signals are forwarded from a pacing can communicatively coupled to the each electrode of the plurality of electrodes in the each satellite, and wherein the transmitting the pacing signal through the plurality of electrodes involves is performed using the pacing can as a signal source and the plurality of electrodes on the each one of the at least one satellite as a signal sink.

11. The method of claim 9, wherein the selecting the at least one electrode based on the cardiac response comprises selecting the at least one electrode through which the pacing signal resulting in a cardiac contraction is transmitted.

12. The method of claim 1, wherein performing the third set of iteration comprises:
    iteratively transmitting a pacing signal through the at least one electrode on the each one of the at least one satellite, wherein the transmitting the pacing signal is performed with a different timing configuration; and
    selecting the at least one pacing signal timing configuration based on a cardiac response resulting from the pacing signal through the at least one electrode on the each one of the at least one satellite.

13. The method of claim 12, wherein the transmitting the pacing signal through the at least one electrodes comprises:
    transmitting a first pulse through a first one of the at least one electrode at a first location, and
    transmitting a second pulse through a second one of the at least one electrode at a second location,
    wherein the at least one timing configuration includes a time delay between the first pulse and the second pulse.

14. The method of claim 12, wherein the iteratively transmitting the pacing signal through the at least one electrode comprises performing a set of coarse-granularity iterations and a set of fine-granularity iterations, and wherein a timing-configuration difference between the coarse-granularity iterations is larger than a timing-configuration difference between the fine-granularity iterations.

15. The method of claim 14, wherein the timing-configuration difference between the coarse-granularity iterations is approximately five to ten times of the timing-configuration difference between the fine-granularity iterations.

16. The method of claim 14, wherein the timing-configuration difference between the coarse-granularity iterations is at least twice the timing-configuration difference between the fine-granularity iterations.

17. The method of claim 14, wherein the timing-configuration difference between the coarse-granularity iterations is approximately five to ten milliseconds, and wherein the timing-configuration difference between the fine-granularity iterations is approximately one millisecond.

18. The method of claim 14, wherein the selecting the at least one timing configuration based on the cardiac response comprises measuring a synchrony corresponding to each one of the at least one timing configuration, wherein after the coarse-granularity iterations, selecting the at least one timing configuration further comprises determining a collection of timing configurations that produce better synchrony than other timing configurations, and wherein the fine-granularity iterations are performed based on the collection of timing configurations determined after the coarse-granularity iterations.

19. The method of claim 18, wherein the determining the collection of timing configurations comprises identifying a broad peak based on a synchrony-versus-timing plot.

20. The method of claim 18, wherein the determining the collection of timing configurations comprises grouping the timing configurations based on a predetermined threshold.

21. The method of claim 18, wherein the measuring the synchrony comprises measuring a time difference between two response signals indicating a cardiac contraction at two corresponding locations.

22. The method of claim 21, wherein the measuring the time difference between the two response signals comprises comparing corresponding highest-slew-rate points of the two signals.

23. The method of claim 18, wherein the measuring the synchrony involves computing a cross-relation of two response signals indicating a cardiac contraction at two corresponding locations.

24. The method of claim 18, wherein the measuring the synchrony involves comparing electromechanical delays of two response signals indicating a cardiac contraction at two corresponding locations.

25. The method of claim 24, wherein the electromechanical delay of a signal is a time delay between a characteristic point of an electrocardiogram (ECG) and a characteristic point of the signal.

26. The method of claim 25, wherein the characteristic point of the ECG is a start of a QRS complex, and wherein the characteristic point of the signal is a corresponding peak of the signal.

27. The method of claim 18, wherein the selecting the at least one timing configuration comprises displaying an illustration of the synchrony corresponding to the timing configuration.

28. The method of claim 27, wherein the displaying the illustration of the synchrony comprises tracing a point in real time on an X-Y coordinate plane, wherein an X coordinate of the point indicates a value corresponding to an amplitude of a first response signal indicating a cardiac contraction at a first location, and wherein a Y coordinate of the point indicates a value corresponding to an amplitude of a second response signal indicating a cardiac contraction at a second location.

29. The method of claim 27, wherein the displaying the illustration of the synchrony comprises:
    tracing a first point on a polar coordinate plane, wherein a radial coordinate of a first point indicates a value corresponding to an amplitude of a first signal indicating a cardiac contraction at a first location, and wherein an angular coordinate of the first point is configured to change at a constant rate;
    tracing a second point on the polar coordinate plane, wherein a radial coordinate of a second point indicates a value corresponding to an amplitude of a second signal indicating a cardiac contraction at a second location, wherein an angular coordinate of the second point is configured to change at the constant rate; and
    highlighting an area enclosed by both traces of the first point and the second point.

30. The method of claim 1, further comprising using a scripting language to automatically execute the performing the first set of iterations, the performing the second set of iterations, and the performing the third set of iterations.

31. The method of claim 30, further comprising saving values for response signals during the performing the first set of iterations, the performing the second set of iterations, and the performing the third set of iterations.

32. The method of claim 31, further comprising loading the values using the scripting language.

33. The method of claim 30, further comprising saving addresses for the at least one satellite and the at least one electrode on the each one of the at least one satellite and the at least one timing configuration using the scripting language.

34. The method of claim 33, further comprising loading the addresses for at least one satellite and the at least one electrode and the at least one timing configuration using the scripting language.

35. The method of claim 30, further comprising generating pacing procedures when the at least one satellite, the at least one electrode, and the at least one timing configuration are specified.

36. The method of claim 35, wherein the generating the pacing procedures comprises generating scripts that automatically perform the pacing procedures.

\* \* \* \* \*

UNITED STATES PATENT AND TRADEMARK OFFICE
CERTIFICATE OF CORRECTION

| | |
|---|---|
| PATENT NO. | : 8,036,743 B2 |
| APPLICATION NO. | : 11/909786 |
| DATED | : October 11, 2011 |
| INVENTOR(S) | : Savage et al. |

It is certified that error appears in the above-identified patent and that said Letters Patent is hereby corrected as shown below:

In the Drawing Fig. 10, should be replaced with the correct Fig. 10 as shown on the attached pages.

In the Drawing Fig. 26, should be replaced with the correct Fig. 26 as shown on the attached pages.

At column 21, line 45, claim 1, of the printed patent, please delete the word "pacing".

At column 22, line 51, claim 12, of the printed patent, should read --third set of iterations comprises--.

At column 22, line 55, claim 12, of the printed patent, please delete the words "pacing signal".

At column 22, line 61, claim 13, of the printed patent, please change "electrodes" to --electrode--.

Signed and Sealed this
Twenty-sixth Day of June, 2012

David J. Kappos
*Director of the United States Patent and Trademark Office*